United States Patent
Cai et al.

(10) Patent No.: US 7,235,674 B2
(45) Date of Patent: Jun. 26, 2007

(54) SUBSTITUTED COUMARINS AND QUINOLINES AND ANALOGS AS ACTIVATORS OF CASPASES AND INDUCERS OF APOPTOSIS AND THE USE THEREOF

(75) Inventors: Sui Xiong Cai, San Diego, CA (US); Hong Zhang, San Diego, CA (US); William E. Kemnitzer, San Diego, CA (US); Songchun Jiang, San Diego, CA (US); John Drewe, Carlsbad, CA (US); Richard Storer, Pinner (GB)

(73) Assignee: Cytovia, Inc., San Diego, CA (US)

( * ) Notice: Subject to any disclaimer, the term of this patent is extended or adjusted under 35 U.S.C. 154(b) by 29 days.

(21) Appl. No.: 10/989,057

(22) Filed: Nov. 16, 2004

(65) Prior Publication Data
US 2005/0090526 A1    Apr. 28, 2005

Related U.S. Application Data

(62) Division of application No. 10/146,136, filed on May 16, 2002, now Pat. No. 7,015,328.

(60) Provisional application No. 60/290,978, filed on May 16, 2001.

(51) Int. Cl.
C07D 311/02    (2006.01)
C07D 311/00    (2006.01)

(52) U.S. Cl. .................... 549/283; 549/285; 549/288

(58) Field of Classification Search ............ 549/283, 549/285, 288; 514/456, 457
See application file for complete search history.

(56) References Cited

U.S. PATENT DOCUMENTS

| | | | |
|---|---|---|---|
| 5,281,619 A | 1/1994 | Dell et al. | |
| 5,284,868 A | 2/1994 | Dell et al. | |
| 5,434,160 A | 7/1995 | Dell et al. | |
| 5,482,967 A * | 1/1996 | Natsugari et al. ........... | 514/457 |
| 5,514,706 A | 5/1996 | Ambler et al. | |
| 5,571,818 A | 11/1996 | Williams | |
| 5,574,034 A | 11/1996 | Williams | |
| 5,576,325 A | 11/1996 | Williams | |
| 5,624,953 A | 4/1997 | Ambler et al. | |
| 5,637,589 A | 6/1997 | Lee et al. | |
| 5,726,204 A | 3/1998 | Lee et al. | |
| 5,847,165 A | 12/1998 | Lee et al. | |
| 6,160,010 A | 12/2000 | Uckun et al. | |
| 6,221,900 B1 | 4/2001 | Uckun et al. | |
| 6,258,824 B1 | 7/2001 | Yang | |
| 6,294,575 B1 | 9/2001 | Uckun et al. | |
| 6,303,652 B1 | 10/2001 | Uckun et al. | |
| 6,365,626 B1 | 4/2002 | Uckun et al. | |
| 6,388,092 B2 | 5/2002 | Yang | |
| 6,858,607 B1 | 2/2005 | Cai et al. | |
| 6,906,203 B1 | 6/2005 | Cai et al. | |

| | | |
|---|---|---|
| 2003/0065018 A1 | 4/2003 | Cai et al. |
| 2005/0165053 A1 | 7/2005 | Cai et al. |
| 2005/0176750 A1 | 8/2005 | Cai et al. |

FOREIGN PATENT DOCUMENTS

| | | |
|---|---|---|
| EP | 0 537 949 A1 | 4/1993 |
| EP | 0 599 514 A2 | 6/1994 |
| EP | 0 618 206 A1 | 10/1994 |
| EP | 0 619 314 A1 | 10/1994 |
| WO | WO 99/54286 | 10/1999 |
| WO | WO 00/47574 A1 | 8/2000 |
| WO | WO 01/34591 A2 | 5/2001 |
| WO | WO 03/096982 A2 | 11/2003 |
| WO | WO 03/097805 A2 | 11/2003 |

OTHER PUBLICATIONS

Bakulev, CA 120:106259, abstract only of Khimiya Geterot. Soedin, 1993, fol 3, pp. 338-348.*
Karandashova, CA 120:106290, abstract only of Khimiya Geterot Soedin, vol. 3, pp. 349-352, 1993.*
El-Agrody, CA 120:244555, abstract only of J of Chem SOc of Pakistan, vol. 15(4), pp. 261-263, 1993.*
Alberola, CA 136:216669, abstract only of Synthesis, vol. 13, pp. 1941-1948, 2001.*
Shatalov, CA 81:4611, absrtact of DE 2224388, 1973.*
Moorty, CA 80:37037, abstract only of Indian J of Chemistry, vol. 11(9), pp. 854-856, 1973.*
Holmbert, CA 69:86762, abstract only of Acta Chemica Scandinavica, 1947-1973, vol. 22(3), pp. 995-1003, 1968.*
Ziegler, CA 68:12832, abstract only Monatshefte fuer Chemie, vol. 96(4), pp. 1252-1260, 1965.*
Borsche, CA 45:8763, Abstract only of Ann. vol. 569, pp. 81-96, 1950.*
Al-Mousawi, S.M., et al., "Synthesis of New Condensed 2-Amino-4H-Pyran-3-Carbonitriles and of 2-Aminoquinoline-3-Carbonitriles," *Organic Preparations and Procedures Int.* 31:305-313, Organic Preparations and Procedures Inc. (1999).

(Continued)

*Primary Examiner*—D. Margaret Seaman
(74) *Attorney, Agent, or Firm*—Sterne, Kessler, Goldstein & Fox P.L.L.C.

(57) ABSTRACT

The present invention is directed to substituted coumarins and quinolines and analogs thereof, represented by the general Formula I:

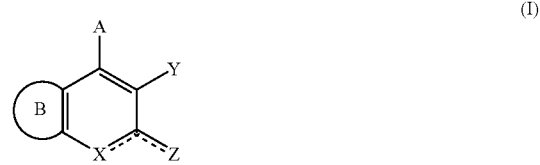

(I)

wherein A, B, X, Y, and Z are defined herein. The present invention also relates to the discovery that compounds having Formula I are activators of caspases and inducers of apoptosis. Therefore, the activators of caspases and inducers of apoptosis of this invention can be used to induce cell death in a variety of clinical conditions in which uncontrolled growth and spread of abnormal cells occurs.

1 Claim, No Drawings

OTHER PUBLICATIONS

Birch, K.A., et al., "LY290181, an Inhibitor of Diabetes-Induced Vascular Dysfunction, Blocks Protein Kinase C-Stimulated Transcriptional Activation Through Inhibition of Transcription Factor Binding to a Phorbol Response Element," *Diabetes 45*:642-650, The American Diabetes Association (1996).

Bloxham, J., et al., "Preparation of Some New Benzylidenemalononitriles by an $S_NAr$ Reaction: Application to Naphtho[1,2-*b*]pyran Synthesis," *Heterocycles 38*:399-408, The Japan Institute of Heterocyclic Chemistry (1994).

Chandrasekhar, S., et al., "Identification of a Novel Chemical Series That Blocks Interleukin-1-Stimulated Metalloprotease Activity in Chrondrocytes," *J. Pharmacol. Exp. Ther. 273*:1519-1528, The American Society for Pharmacology and Experimental Therapeutics (1995).

Chemical Abstracts, vol. 99, No. 27, Abstract 212393z (1983).

Chemical Abstracts, vol. 125, No. 21, Abstract 265467p (1996).

Elagamey, A.G.A., et al., "Nitriles in Heterocyclic Synthesis: Novel Syntheses of Benzo[*b*]pyrans, Naphtho[1,2-*b*]pyrans, Naphtho[2,1-*b*]pyrans, Pyrano[3,2-*h*]quinolines and Pyrano[3,2-*c*]quinolines," *Collection Czechoslovak Chem. Commun. 53*:1534-1538, Institute of Organic Chemistry and Biochemistry (1988).

Greenwald, R.B., "Drug Delivery Systems Employing 1,4- or 1,6-Elimination: Poly(ethylene glycol) Prodrugs of Amine-Containing Compounds," *J. Med. Chem. 42*:3657-3667, American Chemical Society (1999).

International Search Report for International Application No. PCT/US02/15401, mailed Sep. 27, 2002.

Klokol, G.V., et al., "Cyclization of Nitriles. XXIII. Addition of Active Phenols to Electron-Deficient Ethylenes, Accompanied by Cyclization to 2-Amino-4H-Benzo[b]pyrans. Crystal Structure of 2-Amino-4-(2-Fluorophenyl)-3-Ethoxycarbonyl-4H-Naphtho[2,1-*b*]pyran," *J. Org. Chem. USSR 23*:369-377, Plenum Publishing Corporation (1987).

Leu, Y.-L., et al., "Design and Synthesis of Water-Soluble Glucuronide Derivatives of Camptothecin for Cancer Prodrug Monotherapy and Antibody-Directed Enzyme Prodrug Therapy (ADEPT)," *J. Med. Chem. 42*:3623-3628, American Chemical Society (1999).

Radwan, S.M., et al., "Synthesis and Some Reactions of New Benzo[*b*]pyran Derivatives," *Phosphorus, Sulfur, and Silicon 101*:207-211, Gordon and Breach Science Publishers SA (1995).

Sharanin, Y.A., and Klokol, G.V., "Synthesis of 2-Amino-4H-Chromenes," *J. Org. Chem. USSR 19*:1582-1583, Plenum Publishing Corporation (1984).

Smith, C.W., et al., "The Anti-Rheumatic Potential of a Series of 2,4-Di-Substituted-4H-Naphtho[1,2-b]pyran-3-Carbonitriles," *Bioorg. Med. Chem. Lett. 5*:2783-2788, Elsevier Science Ltd. (1995).

Wiernicki, T.R., et al., "Inhibition of Vascular Smooth Muscle Cell Proliferation and Arterial Intimal Thickening by a Novel Antiproliferative Naphthopyran," *J. Pharmacol. Exp. Ther. 278*:1452-1459, The American Society for Pharmacology and Experimental Therapeutics (1996).

Wood, D.L., et al., "Inhibition of Mitosis and Microtubule Function through Direct Tubulin Binding by a Novel Antiproliferative Naphthopyran LY290181," *Mol. Pharmacol. 52*:437-444, The American Society for Pharmacology and Experimental Therapeutics (1997).

Pending Non-Provisional U.S. Appl. No. 10/514,427, Cai et al., filed Nov. 16, 2004 (Not Published).

Gordeau, H., et al., "Antivascular and antitumor evaluation of 2-amino-4-(3-bromo-4,5-dimethoxy-phenyl)-3-cyano-4H-chromenes, a novel series of anticancer agents," *Mol. Cancer Ther., 3*:1375-1383, American Association for Cancer Research (2004).

Kasibhatla, S., et al., "Discovery and mechanism of action of a novel series of apoptosis inducers with potential vascular targeting activity," *Mol. Cancer Ther., 3*:1365-1373, American Association for Cancer Research (2004).

Kemnitzer, W., et al., "Discovery of 4-Aryl-4H-chromenes as a New Series of Apoptosis Inducers Using a Cell- and Caspase-based High-Throughput Screening Assay. 1. Structure-Activity Relationships of the 4-Aryl Group," *J. Med. Chem., 47*:6299-6310, American Chemical Society (2004).

Bundgaard, H., "5. Design and Application of Prodrugs," in: *Textbook of Drug Design and Development,* Krogsgaard-Larsen and Bundgaard, H., eds., Hardwood Academic Publishers, Philadelphia, PA, pp. 113-135 (1991).

Kemnitzer, W., et al., "Discovery of 4-aryl-4H-chromenes as a new series of apoptosis inducers using a cell- and caspase-based high-throughput screening assay. 2. Structure-activity relationships of the 7- and 5-, 6-, 8-positions," *Bioorg. Med. Chem. Lett. 15*:4745-4751, Elsevier Ltd. (Sep. 2005).

* cited by examiner

SUBSTITUTED COUMARINS AND QUINOLINES AND ANALOGS AS ACTIVATORS OF CASPASES AND INDUCERS OF APOPTOSIS AND THE USE THEREOF

CROSS-REFERENCE TO RELATED APPLICATIONS

This is a Divisional Application of U.S. patent application Ser. No. 10/146,136, filed May 16, 2002 now U.S. Pat. No. 7,015,328, which claims priority benefit under 35 U.S.C. § 119(e) of U.S. Provisional Application No. 60/290,978, filed May 16, 2001, both of which are incorporated herein by reference in their entirety for all purposes.

BACKGROUND OF THE INVENTION

1. Field of the Invention

This invention is in the field of medicinal chemistry. In particular, the invention relates to substituted coumarins and quinolines and analogs, and the discovery that these compounds are activators of caspases and inducers of apoptosis. The invention also relates to the use of these compounds as therapeutically effective anti-cancer agents.

2. Description of Background Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO 96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal and cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al, *Nat. Med.* 2:574 (1996)). The mechanism of action of current antineoplastic drugs frequently involves an attack at specific phases of the cell cycle. In brief, the cell cycle refers to the stages through which cells normally progress during their lifetimes. Normally, cells exist in a resting phase termed $G_o$. During multiplication, cells progress to a stage in which DNA synthesis occurs, termed S. Later, cell division, or mitosis occurs, in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, for example colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, N.Y. (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

SUMMARY OF THE INVENTION

The present invention is related to the discovery that substituted coumarins and quinolines and analogs, as represented in Formula I, are activators of the caspase cascade and inducers of apoptosis. Thus, an aspect of the present invention is directed to the use of compounds of Formula I as inducers of apoptosis.

A second aspect of the present invention is to provide a method for treating, preventing or ameliorating neoplasia and cancer by administering a compound of Formula I to a mammal in need of such treatment.

Many of compounds within the scope of the present invention are novel compounds. Therefore, a third aspect of the present invention is to provide novel compounds of Formula I, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A fifth aspect of the present invention is directed to methods for the preparation of novel compounds of Formula I.

A sixth aspect of the present invention is directed to a process for the preparation of a compound having Formula III

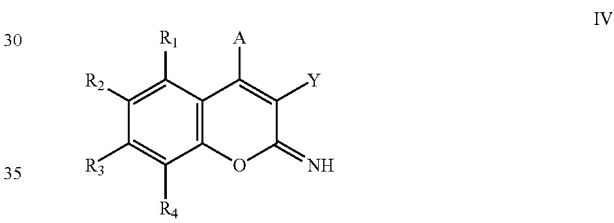

the process comprising reacting a 2-aminobenzopyran having the formula:

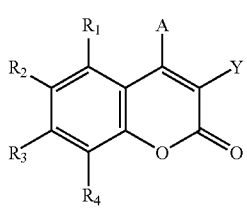

wherein Y is CN, COR$_7$, CO$_2$R$_7$ or CONR$_x$R$_y$, wherein R$_7$, R$_x$ and R$_y$ are independently hydrogen, C$_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or R$_x$ and R$_y$ are taken together with the nitrogen to which they are attached to form a heterocycle;

A is optionally substituted and is aryl, heteroaryl, saturated carbocyclic, partially saturated carbocylic, saturated heterocyclic, partially saturated heterocyclic, arylalkyl or heteroarylalkyl; and R$_1$-R$_4$ are independently hydrogen, halo, haloalkyl, aryl, fused aryl, carbocyclic, a heterocyclic group, a heteroaryl group, C$_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or R$_1$ and R$_2$, or R$_2$ and R$_3$, or R$_3$ and R$_4$, taken together with the atoms to which they are attached form an aryl, heteroaryl, partially saturated carbocyclic or partially saturated heterocyclic group, wherein said group is optionally substituted;

with an oxidant in an organic solvent to produce a 2-imino-2H-chromene of Formula IV:

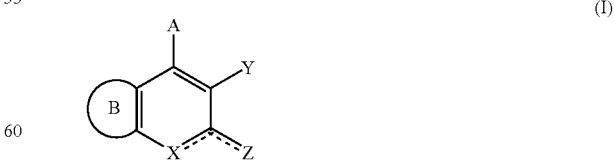

contacting said 2-imino-2H-chromene with an aqueous acid, and isolating the product of Formula III.

DETAILED DESCRIPTION OF THE INVENTION

The present invention arises out of the discovery that substituted coumarins and quinolines and analogs, as represented in Formula I, are potent and highly efficacious activators of the caspase cascade and inducers of apoptosis. Therefore compounds of Formula I are useful for treating disorders responsive to induction of apoptosis.

Specifically, compounds useful in this aspect of the present invention are represented by Formula I:

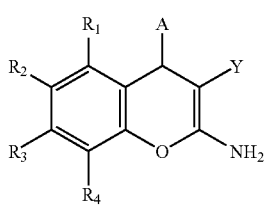

or pharmaceutically acceptable salts or prodrugs thereof, wherein:
the dashed lines cannot both be a double bond at the same time;

X is O, S or NR$_6$, wherein R$_6$ is hydrogen or optionally substituted alkyl or aryl;

Y is CN, COR$_7$, CO$_2$R$_7$ or CONR$_x$R$_y$, wherein R$_7$, R$_x$ and R$_y$ are independently hydrogen, C$_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or R$_x$ and R$_y$ are taken together with the nitrogen to which they are attached to form a heterocycle;

Z is O, S, halo, NR$_8$, or NCOR$_8$, wherein R$_8$ is independently H, C$_{1-4}$ alkyl or aryl;

A is optionally substituted and is aryl, heteroaryl, saturated carbocyclic, partially saturated carbocyclic, saturated heterocyclic, partially saturated heterocyclic, arylalkyl or heteroarylalkyl; and B is optionally substituted and is an aryl, heteroaryl, saturated carbocyclic, partially saturated carbocyclic, saturated heterocyclic, or partially saturated heterocyclic ring.

Preferred compounds have Formula IIA:

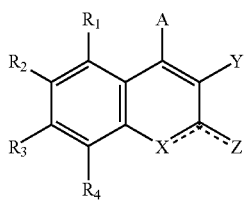

IIA or pharmaceutically acceptable salts or prodrugs thereof, wherein:

X, Y, Z and A are defined above with respect to Formula (I), and

R$_1$-R$_4$ are independently hydrogen, halo, haloalkyl, aryl, fused aryl, carbocyclic, a heterocyclic group, a heteroaryl group, C$_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or R$_1$ and R$_2$, or R$_2$ and R$_3$, or R$_3$ and R$_4$, taken together with the atoms to which they are attached form an aryl, heteroaryl, partially saturated carbocyclic or partially saturated heterocyclic group, wherein said group is optionally substituted.

Particularly preferred are compounds having Formula IIB:

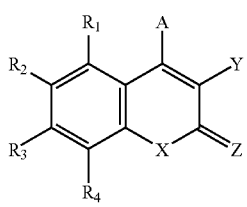

IIB where the substituents are defined above with respect to Formula IIA.

Preferred are compounds of Formulae IIA and IIB (hereinafter Formula II), wherein R$_1$ and R$_2$, or R$_2$ and R$_3$, or R$_3$ and R$_4$, taken together form a structure selected from the group consisting of —OCH$_2$O—, —(CH$_2$)$_3$—, —(CH$_2$)$_4$—, —CH$_2$C(V)$_2$O—, —OCH$_2$CH$_2$O—, —CH$_2$N(V)CH$_2$—, —CH$_2$CH$_2$N(V)CH$_2$—, —CH$_2$N(V)CH$_2$CH$_2$—, —N(V)—CH=CH—, CH=CH—N(V)—, —N(V)—CH=N—, —N=CH—O—, —N(V)—CH=N—, —O—CH=N—, —N=CH—O—, —S—CH=N—, —N=CH—S—, —O—CH=CH—, —CH=CH—O—, —S—CH=CH—, —CH=CH—S, —CH=CH—CH=CH—, —N=CH—CH=CH—, —CH=N—CH=CH—, —CH=CH—N=CH—, —CH=CH—CH=N—, —N=CH—CH=N—, —NH—CH$_2$—NH—, —NH—CO—NH—, —N—CO—CO—N—, —N—CH$_2$—CH$_2$—N—, and —N=N—NH—, wherein V is hydrogen, C$_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl. Especially preferred compounds of Formula II are wherein R$_3$ and R$_4$ together form an optionally substituted ring, wherein said ring is selected from the group consisting of benzo, pyrido, furo, dihydrofuro, thieno, pyrrolo, imidazolo, pyrazo, thiazolo, oxazolo, 2-oxadihydroimidazolo, 1,4-dihydropyrazine-2,3-dione, imidazolino, imidazol-2-one, imidazol-2-thion, oxazol-2-one, triazolo, or piperazo ring.

Preferred compounds falling within the scope of Formula II also include compounds wherein R$_1$-R$_4$ are independently hydrogen, halogen, hydroxy, C$_{1-10}$ alkyl, hydroxyalkyl, aminoalkyl, carboxyalkyl, amino, acylamido, acyloxy, alkoxy, methylenedioxy or alkylthiol; X is O, S or N; Z is O, Cl or NH, and Y is CN.

Preferred compounds of Formula IIA are substituted chromenes and quinolines and analogs represented by Formulae III-VI:

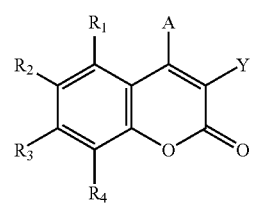

III

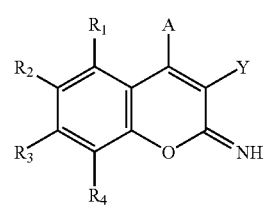

IV

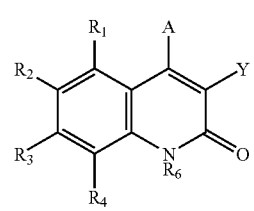

V

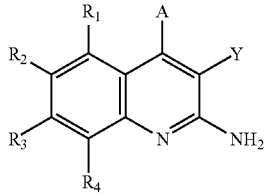

or pharmaceutically acceptable salts or prodrugs thereof, wherein $R_1$-$R_4$, $R_6$, Y and A are as defined previously with respect to Formulae I and II.

Additional preferred compounds of Formula IIA are substituted quinolines and analogs represented by Formula VII:

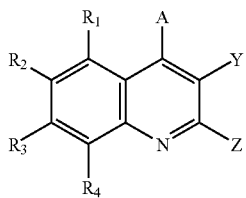

or pharmaceutically acceptable salts or prodrugs thereof, wherein $R_1$-$R_4$, Y and are as defined previously with respect to Formulae I and II, and Z is halo.

Preferred compounds falling within the scope of Formulae II-VII include compounds wherein $R_1$-$R_2$ are hydrogen. Preferably Y is CN. Preferably A is optionally substituted phenyl, naphthyl, pyridyl, quinolyl, isoquinolyl, thienyl, furyl, pyrrolyl, 2-phenylethyl or cyclohexyl. More preferably, A is

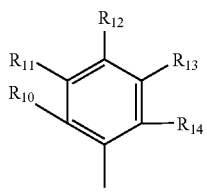

wherein $R_{10}$-$R_{14}$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol.

Also preferred A includes where $R_{10}$ and $R_{11}$, or $R_{11}$ and $R_{12}$, taken together with the atoms to which they are attached form an aryl, heteroaryl, optionally substituted carbocyclic or optionally substituted heterocyclic group, wherein said group is optionally substituted. In a more preferred embodiment, $R_{10}$ and $R_{11}$, or $R_{11}$ and $R_{12}$, are taken together to form a structure selected from the group consisting of —OCH$_2$O—, —(CH$_2$)$_3$—, —(CH$_2$)$_4$—, —OCH$_2$CH$_2$O—, —CH$_2$N(V)CH$_2$—, —CH$_2$CH$_2$N(V)CH$_2$—, —CH$_2$N(V)CH$_2$CH$_2$—, —CH═CH—CH═CH—, —N(V)—CH═CH—, —CH═CH—N(V)—, —O—CH═CH—, —CH═CH—O—, —S—CH═CH—, —CH═CH—S—, —N═CH—CH═CH—, —CH═N—CH═CH—, —CH═CH—N═CH—, —CH═CH—CH═N— and —N═CH—CH═N—, wherein V is hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Exemplary preferred compounds that may be employed in the method of the invention include, without limitation:

3-Cyano-7-methoxy-4-(3-bromo-4,5-dimethoxyphenyl)-2-oxo-2H-chromene;
3-Cyano-7-methoxy-4-(3,5-dimethoxyphenyl)-2-oxo-2H-chromene;
3-Cyano-4-(3-methoxyphenyl)-2-oxo-2H-pyrrolo[2,3-h]chromene;
3-Cyano-4-phenyl-quinolin-1H-2-one;
3-Cyano-7-methoxy-4-(3-methoxy-phenyl)quinolin-1H-2-one;
7-Chloro-3-cyano-4-(3-methoxyphenyl)-quinolin-1H-2-one;
4-(3-Bromo-4,5-dimethoxy-phenyl)-3-cyano-7-methoxy-quinolin-1H-2-one;
3-Cyano-2-imino-4-(5-methyl-pyridin-3-yl)-2H-pyrrolo[2,3-h]chromene;
3-Cyano-2-imino-7-methyl-4-(5-methyl-pyridin-3-yl)-2H-pyrrolo[2,3-h]chromene;
4-(3-Bromo-4,5-dimethoxy-phenyl)-3-cyano-2-imino-7-methyl-2H-pyrrolo[2,3-h]chromene;
3-Cyano-4-(5-methyl-pyridin-3-yl)-2-oxo-2H-pyrrolo[2,3-h]chromene;
3-Cyano-4-(5-methyl-pyridin-3-yl)-7-methyl-2-oxo-2H-pyrrolo[2,3-h]chromene;
4-(3-Bromo-4,5-dimethoxy-phenyl)-3-cyano-7-methyl-2-oxo-2H-pyrrolo[2,3-h]chromene;
4-(3,5-Dimethoxyphenyl)-3-cyano-2-oxo-2H-pyrrolo[2,3-h]chromene;
3-Cyano-4-(3-methoxy-phenyl)-7-methoxy-2-oxo-2H-chromene;
7-Amino-4-(3-bromo-4,5-dimethoxyphenyl)-3-cyano-2-oxo-2H-chromene;
2-Amino-4-(3-bromo-4,5-dimethoxyphenyl)-3-cyano-5,6-dihydro-benzo[h]quinoline;
4-(3-Bromo-4,5-dimethoxyphenyl)-3-cyano-7,8-dihydro-8,8-dimethyl-2-oxo-2H-furo[3,2-h]chromene;
3-Cyano-7-dimethylamino-4-(3-bromo-4,5-dimethoxyphenyl)-2-oxo-2H-chromene;
7-Amino-3-cyano-4-(3,5-dimethoxyphenyl)-2-oxo-2H-chromene;
3-Cyano-7-dimethylamino-4-(3,5-dimethoxyphenyl)-2-oxo-2H-chromene;
3-Cyano-4-(2,5-dimethoxyphenyl)-2-oxo-2H-pyrrolo[2,3-h]chromene;
4-(3-Bromo-4,5-dimethoxy-phenyl)-3-cyano-7-methylamino-2-oxo-2H-chromene;
7-Amino-4-(3-bromo-4,5-dimethoxy-phenyl)-3-cyano-2-imino-2H-chromene;
7-Bromo-4-(3-bromo-4,5-dimethoxy-phenyl)-3-cyano-2-imino-2H-chromene;
4-(3-Bromo-4,5-dimethoxy-phenyl)-7-chloro-3-cyano-2-oxo-2H-chromene;
4-(3-Bromo-4,5-dimethoxy-phenyl)-7-chloro-3-cyano-2-imino-2H-chromene;
2-Imino-3-cyano-7-methoxy-4-(3'-methoxy-phenyl)-2H-thiochromene;

2-Imino-3-cyano-7-dimethylamino-4-(3-bromo-4,5-dimethoxy-phenyl)-2H-chromene;
3-Cyano-2-imino-7-methyl-4-(3-nitro-phenyl)-2H-pyrrolo[2,3-h]chromene;
3-Cyano-2-imino-7-methyl-4-(3,4,5-trimethoxy-phenyl)-2H-pyrrolo[2,3-h]chromene;
3-Cyano-4-(3,5-dimethoxy-phenyl)-2-imino-7-methyl-2H-pyrrolo[2,3-h]chromene;
3-Cyano-2-imino-4-(3-methoxy-4,5-methylenedioxyphenyl)-7-methyl-2H-pyrrolo[2,3-h]chromene;
3-Cyano-2-imino-4-(3-methoxy-phenyl)-7-methyl-2H-pyrrolo[2,3-h]chromene;
3-Cyano-2-imino-4-(3-bromophenyl)-7-methyl-2H-pyrrolo[2,3-h]chromene;
3-Cyano-7-methyl-4-(3-nitro-phenyl)-2-oxo-2H-pyrrolo[2,3-h]chromene;
3-Cyano-4-(3,5-dimethoxy-phenyl)-7-methyl-2-oxo-2H-pyrrolo[2,3-h]chromene;
3-Cyano-4-(3-methoxy-4,5-methylenedioxyphenyl)-7-methyl-2-oxo-2H-pyrrolo[2,3-h]chromene;
3-Cyano-4-(3-methoxy-phenyl)-7-methyl-2-oxo-2H-pyrrolo[2,3-h]chromene;
3-Cyano-4-(3-bromo-phenyl)-7-methyl-2-oxo-2H-pyrrolo[2,3-h]chromene; and
3-Cyano-7-methyl-4-(3,4,5-trimethoxy-phenyl)-2-oxo-2H-pyrrolo[2,3-h]chromene.

The present invention is also directed to novel compounds within the scope of Formulae I-VII.

Exemplary preferred novel compounds of this invention include, without limitation:
3-Cyano-7-methoxy-4-(3-bromo-4,5-dimethoxyphenyl)-2-oxo-2H-chromene;
3-Cyano-7-methoxy-4-(3,5-dimethoxyphenyl)-2-oxo-2H-chromene;
3-Cyano-4-(3-methoxyphenyl)-2-oxo-2H-pyrrolo[2,3-h]chromene;
3-Cyano-4-phenyl-quinolin-1H-2-one;
3-Cyano-7-methoxy-4-(3-methoxy-phenyl)quinolin-1H-2-one;
7-Chloro-3-cyano-4-(3-methoxyphenyl)-quinolin-1H-2-one;
4-(3-Bromo-4,5-dimethoxy-phenyl)-3-cyano-7-methoxy-quinolin-1H-2-one;
3-Cyano-2-imino-4-(5-methyl-pyridin-3-yl)-2H-pyrrolo[2,3-h]chromene;
3-Cyano-2-imino-7-methyl-4-(5-methyl-pyridin-3-yl)-2H-pyrrolo[2,3-h]chromene;
4-(3-Bromo-4,5-dimethoxy-phenyl)-3-cyano-2-imino-7-methyl-2H-pyrrolo[2,3-h]chromene;
3-Cyano-4-(5-methyl-pyridin-3-yl)-2-oxo-2H-pyrrolo[2,3-h]chromene;
3-Cyano-4-(5-methyl-pyridin-3-yl)-7-methyl-2-oxo-2H-pyrrolo[2,3-h]chromene;
4-(3-Bromo-4,5-dimethoxy-phenyl)-3-cyano-7-methyl-2-oxo-2H-pyrrolo[2,3-h]chromene;
4-(3,5-Dimethoxyphenyl)-3-cyano-2-oxo-2H-pyrrolo[2,3-h]chromene;
3-Cyano-4-(3-methoxy-phenyl)-7-methoxy-2-oxo-2H-chromene;
7-Amino-4-(3-bromo-4,5-dimethoxyphenyl)-3-cyano-2-oxo-2H-chromene;
2-Amino-4-(3-bromo-4,5-dimethoxyphenyl)-3-cyano-5,6-dihydro-benzo[h]quinoline;
4-(3-Bromo-4,5-dimethoxyphenyl)-3-cyano-7,8-dihydro-8,8-dimethyl-2-oxo-2H-furo[3,2-h]chromene;
3-Cyano-7-dimethylamino-4-(3-bromo-4,5-dimethoxyphenyl)-2-oxo-2H-chromene;
7-Amino-3-cyano-4-(3,5-dimethoxyphenyl)-2-oxo-2H-chromene;
3-Cyano-7-dimethylamino-4-(3,5-dimethoxyphenyl)-2-oxo-2H-chromene;
3-Cyano-4-(2,5-dimethoxyphenyl)-2-oxo-2H-pyrrolo[2,3-h]chromene;
4-(3-Bromo-4,5-dimethoxy-phenyl)-3-cyano-7-methylamino-2-oxo-2H-chromene;
7-Amino-4-(3-bromo-4,5-dimethoxy-phenyl)-3-cyano-2-imino-2H-chromene;
7-Bromo-4-(3-bromo-4,5-dimethoxy-phenyl)-3-cyano-2-imino-2H-chromene;
4-(3-Bromo-4,5-dimethoxy-phenyl)-7-chloro-3-cyano-2-oxo-2H-chromene;
4-(3-Bromo-4,5-dimethoxy-phenyl)-7-chloro-3-cyano-2-imino-2H-chromene;
2-Imino-3-cyano-7-methoxy-4-(3'-methoxy-phenyl)-2H-thiochromene;
2-Imino-3-cyano-7-dimethylamino-4-(3-bromo-4,5-dimethoxy-phenyl)-2H-chromene;
3-Cyano-2-imino-7-methyl-4-(3-nitro-phenyl)-2H-pyrrolo[2,3-h]chromene;
3-Cyano-2-imino-7-methyl-4-(3,4,5-trimethoxy-phenyl)-2H-pyrrolo[2,3-h]chromene;
3-Cyano-4-(3,5-dimethoxy-phenyl)-2-imino-7-methyl-2H-pyrrolo[2,3-h]chromene;
3-Cyano-2-imino-4-(3-methoxy-4,5-methylenedioxyphenyl)-7-methyl-2H-pyrrolo[2,3-h]chromene;
3-Cyano-2-imino-4-(3-methoxy-phenyl)-7-methyl-2H-pyrrolo[2,3-h]chromene;
3-Cyano-2-imino-4-(3-bromophenyl)-7-methyl-2H-pyrrolo[2,3-h]chromene;
3-Cyano-7-methyl-4-(3-nitro-phenyl)-2-oxo-2H-pyrrolo[2,3-h]chromene;
3-Cyano-4-(3,5-dimethoxy-phenyl)-7-methyl-2-oxo-2H-pyrrolo[2,3-h]chromene;
3-Cyano-4-(3-methoxy-4,5-methylenedioxyphenyl)-7-methyl-2-oxo-2H-pyrrolo[2,3-h]chromene;
3-Cyano-4-(3-methoxy-phenyl)-7-methyl-2-oxo-2H-pyrrolo[2,3-h]chromene;
3-Cyano-4-(3-bromo-phenyl)-7-methyl-2-oxo-2H-pyrrolo[2,3-h]chromene; and
3-Cyano-7-methyl-4-(3,4,5-trimethoxy-phenyl)-2-oxo-2H-pyrrolo[2,3-h]chromene.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which can be optionally substituted.

Useful alkoxy groups include oxygen substituted by one of the $C_{1-10}$ alkyl groups mentioned above, which can be optionally substituted.

Useful alkylthio groups include sulphur substituted by one of the $C_{1-10}$ alkyl groups mentioned above, which can be optionally substituted. Also included are the sulfoxides and sulfones of such alkylthio groups.

Useful amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group can be optionally substituted.

Optional substituents on the alkyl groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_6$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl. Optional substituents on the aryl, heteroaryl, saturated carbocyclic, partially saturated carbocyclic, saturated heterocyclic, and partially saturated heterocyclic groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy or carboxy.

Useful aryl groups include $C_{6-14}$ aryl, preferably $C_{6-10}$ aryl. Typical $C_{6-14}$ aryl groups include phenyl, naphthyl, 1,2,3,4-tetrahydronaphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-4}$ aryl groups. Preferably the arylalkyl group is benzyl, phenethyl or naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

Useful saturated or partially saturated heterocyclic groups include tetrahydrofuranyl, pyranyl, piperidinyl, piperazinyl, pyrrolidinyl, 2-thio-4-oxo-2,4H-pyrimidyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include thienyl, benzo[b]thienyl, naphtho[2,3-b]thienyl, thianthrenyl, furyl, pyranyl, dihydrobezofuranyl, benzofuranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, thiazolyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-thio-4-oxo-2,4H-pyrimidyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

Some of the compounds of the present invention may exist as stereoisomers including optical isomers. The invention includes all stereoisomers and both the racemic mixtures of such stereoisomers, as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (J. Med. Chem. 42:3623-3628 (1999)) and Greenwald, et. al., (J. Med. Chem. 42:3657-3667 (1999)); acetals and ketals of alcohol containing compounds (e.g., those obtained by condensation with chloromethyl methyl ether or chloromethyl ethyl ether according to methods known in the art); and phosphonato and phosphono compounds (e.g., those obtained by condensation with a phosphate ester, phosphoryl chloride, or phosphoric acid), which include pharmaceutically acceptable mono-basic and di-basic addition salts of the phosphono group, e.g., organic bases such as amine bases, which include ammonia, piperidine and morpholine.

The compounds of this invention may be prepared using methods known to those skilled in the art, or the novel methods of this invention.

Specifically, the compounds of this invention with Formulae III-IV can be prepared as illustrated by exemplary reaction in Scheme 1. Reaction of 2-hydroxybenzophenone with malononitrile in the presence a base such as piperidine produces 3-cyano-2-imino-4-phenyl-2H-chromene. Treatment of the imino-chromene with $HCl/H_2O$ results in hydrolysis of the imino group and produces 3-cyano-4-phenyl-2-oxo-2H-chromene.

SCHEME 1

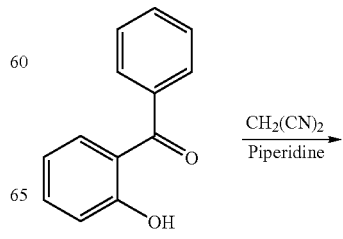

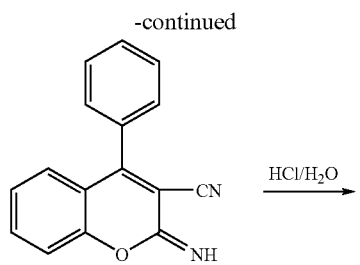

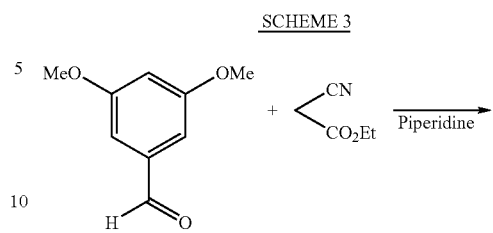

SCHEME 3

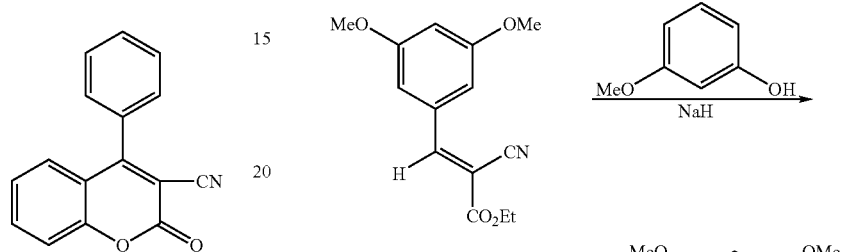

Alternatively, compounds of Formula III can be prepared as shown in Scheme 2. Coupling of 2-hydroxybenzophenone with the acyl chloride produces the ester, which when treated with base such as NaOEt or NaOMe cyclizes to produce 3-cyano-4-phenyl-2-oxo-2H-chromene.

SCHEME 4

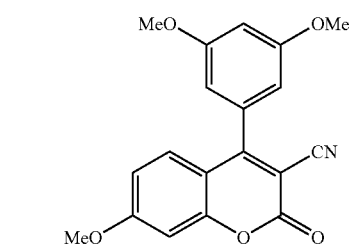

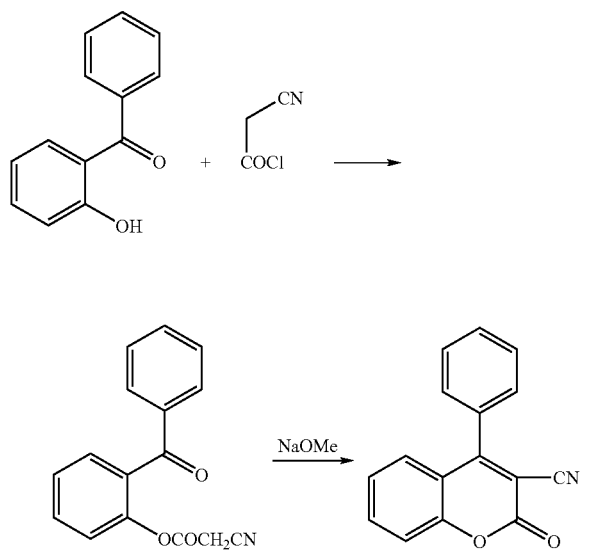

SCHEME 2

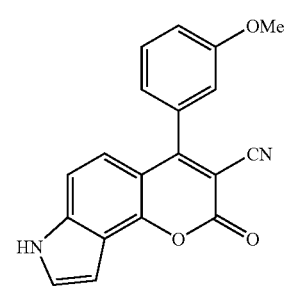

Alternatively, compounds of Formula III can be prepared as shown in Schemes 3 and 4. Condensation of 3,5-dimethoxybenzaldehyde with ethyl cyanoacetate in the presence of a base such as piperidine produces the 3-(3,5-dimethoxyphenyl)-2-cyano-acrylic acid ethyl ester. Treatment of the ester with 3-methoxyphenol in the presence of NaH produces the 3-cyano-7-methoxy-4-(3,5-dimethoxyphenyl)-2-oxo-2H-chromene. Similarly, reaction of 3-(3-methoxy-phenyl)-2-cyano-acrylic acid ethyl ester with 4-hydroxyindole produces 3-cyano-4-(3-methoxyphenyl)-2-oxo-2H-pyrrolo[2,3-h]chromene.

Compounds of Formula V may be prepared as shown in Scheme 5. Coupling of 2-aminobenzophenone with the acyl chloride produces the amide, which when treated with a base such as NaOEt or NaOMe cyclizes to produce 3-cyano-4-phenyl-quinolin-2(1H)-one.

SCHEME 5

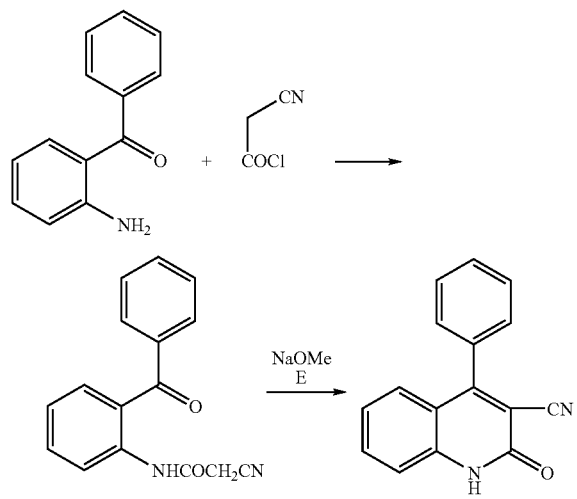

Compounds of Formula VI may be prepared as shown in Scheme 6. Reaction of 2-aminobenzophenone with malononitrile in the presence of a base such as piperidine produces 2-amino-3-cyano-4-phenyl-quinoline.

SCHEME 6

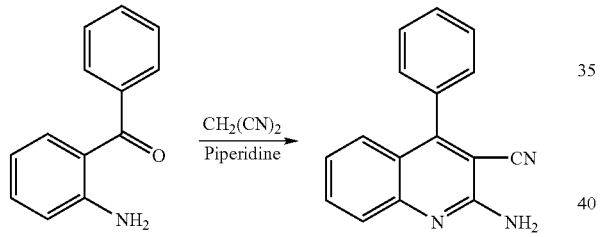

Substituted 2-aminobenzophenones may be prepared as illustrated by exemplary reaction in Scheme 7. The amino group in 3-methoxyaniline may be protected, e.g. by reaction with acetic anhydride to produce the amide. Reaction of the amide with 3-methoxybenzoyl chloride in the presence of AlCl₃ produces the substituted benzophenone. The amide protecting group is removed under acidic condition to produce 2-amnino-4-methoxy-3'-methoxy-benzophenone.

SCHEME 7

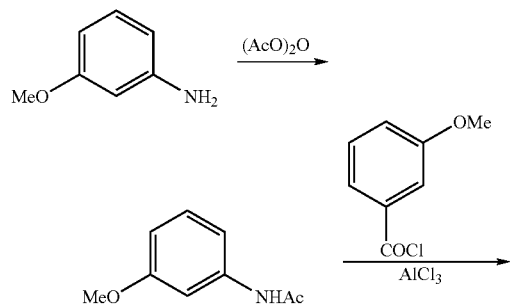

Substituted 2-hydroxybenzophenones may be prepared as illustrated by exemplary reaction in Scheme 8. Reaction of 3-methoxyphenol with 3-methoxybenzoic acid in the presence of Al₂O₃ and CH₃SO₃H produces 2-hydroxy-4-methoxy-3'-methoxy-benzophenone.

SCHEME 8

In an alternative embodiment, the invention relates to a process for the preparation of compounds of Formulae III and IV. The process is illustrated in Scheme 9. The process comprises first oxidizing an optionally substituted 2-aminobenzopyran in an organic solvent to yield a 2-iminobenzopyran. For example, oxidation of 2-amino-3-cyano-4-(5-methyl-pyridin-3-yl)-4H-pyrrolo[2,3-h]chromene using 2,3-dichloro-5,6-dicyano-1,4-benzoquinone (DDQ) in dichloromethane gave 3-cyano-2-imino-4-(5-methyl-pyridin-3-yl)-2H-pyrrolo[2,3-h]chromene (compound of Formula IV).

The process further comprises contacting the 2-iminobenzopyran with an aqueous acid to produce an optionally substituted coumarin (2-oxo-2H-chromene). For example, the hydrolysis of 3-cyano-2-imino-4-(5-methyl-pyridin-3-yl)-2H-pyrrolo[2,3-h]chromene using HCl/H₂O produced 3-cyano-4-(5-methyl-pyridin-3-yl)-2-oxo-2H-pyrrolo[2,3-h]chromene (compound of Formula III).

SCHEME 9

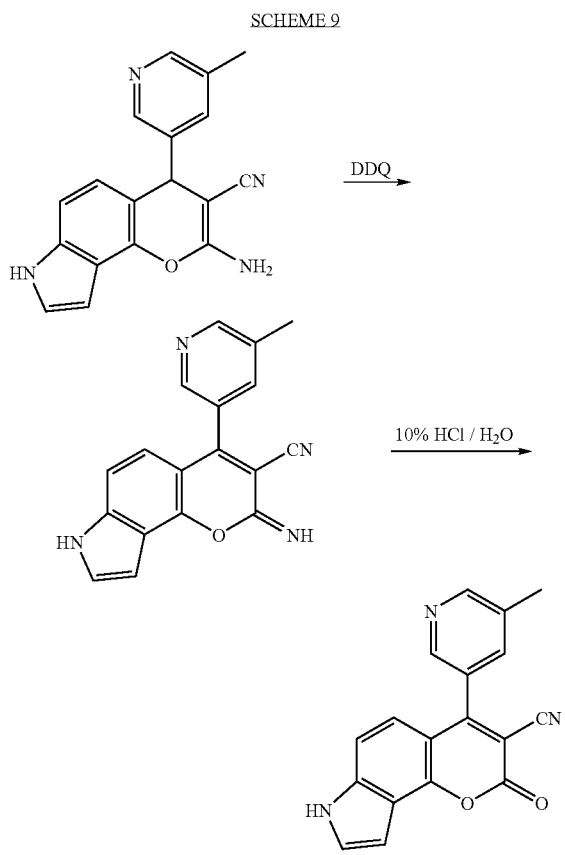

Oxidants for use in the present invention include any oxidant capable of oxidizing the 2-aminobenzopyran into 2-iminobenzopyran. This includes, but is not limited to, 2,3-dichloro-5,6-dicyano-1,4-benzoquinone (DDQ), 2,3,5,6-tetrachloro-1,4-benzoquinone (chlorinal), bromine, fluorine, atmospheric oxygen, manganese dioxide, selenium dioxide, mercuric acetate, palladium (II) salts, such as palladium dichloride, iron (II) and iron (III) salts, such as ferric chloride, copper (II) salts, such as cupric chloride, trifluoracetic acid, activated charcoal, platinum, and palladium.

The oxidation reaction is performed in any organic solvent that is inert to the reaction conditions, for example, dichloromethane, chloroform, carbon tetrachloride, benzene, toluene, xylenes, chlorobenzene, dichlorobenzene, hexanes, heptane and trimethylpentane. The reaction is performed at a temperature that is high enough to effect the oxidation without causing decomposition of the product. For example the reaction is performed at a temperature in the range of approximately 0° C. to approximately 100° C., alternatively from approximately 20° C. to approximately 40° C. Preferably, the oxidation reaction is performed in dichloromethane, using DDQ as oxidant, at room temperature. The product is isolated using procedures well known to those in the art. This includes, for example, but is not limited to, first neutralizing the reaction mixture by washing with aqueous sodium bicarbonate solution. Second, drying the organic layer and evaporating the solvent to yield the crude product. Finally, the product is optionally purified by any method known to those in the art, for example, flash column chromatography.

Acids for use in the hydrolysis of the 2-iminobenzopyrans include, but are not limited to mineral acids, such as sulfuric, nitric, hydrochloric, and hydrobromic acid; other inorganic acids, such as phosphoric acid; and organic acids, such as trichloroacetic and trifluoroacetic acid. The hydrolysis is performed at a temperature in the range of approximately 0° C. to approximately 100° C., alternatively from approximately 20° C. to approximately 40° C. Preferably, the hydrolysis is performed using an aqueous mixture of hydrochloric acid at room temperature. The 2-oxo-4H-chromene product is isolated from the reaction mixture using procedures well known to those in the art. This includes, for example, but is not limited to, first neutralizing the reaction by washing with an aqueous solution of approximately 10% sodium hydroxide. The mixture is extracted with organic solvent, for example, ethyl acetate, and the organic extract is washed with water, dried and evaporated to yield the crude product. Finally, the crude product is optionally purified by any means known to those in the art, for example, flash column chromatography.

Alternatively, compounds of Formula II can be prepared according to Scheme 10.

SCHEME 10

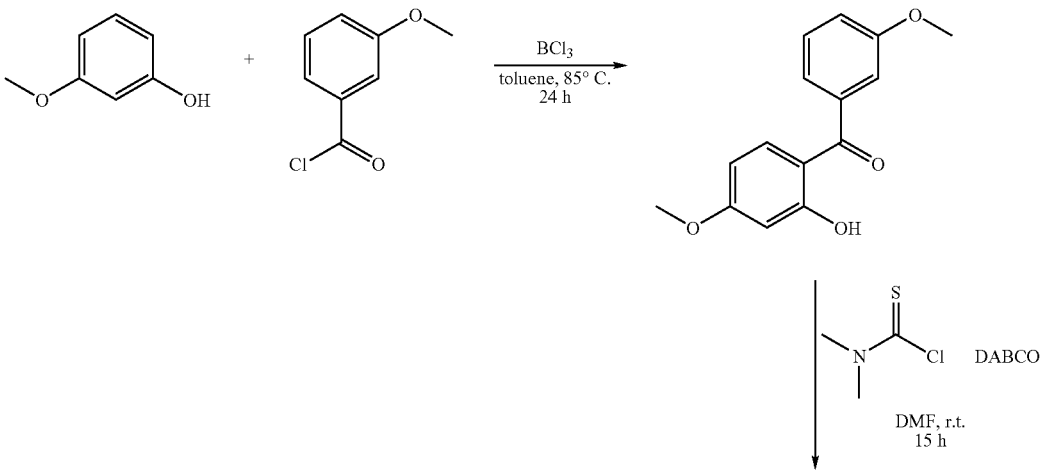

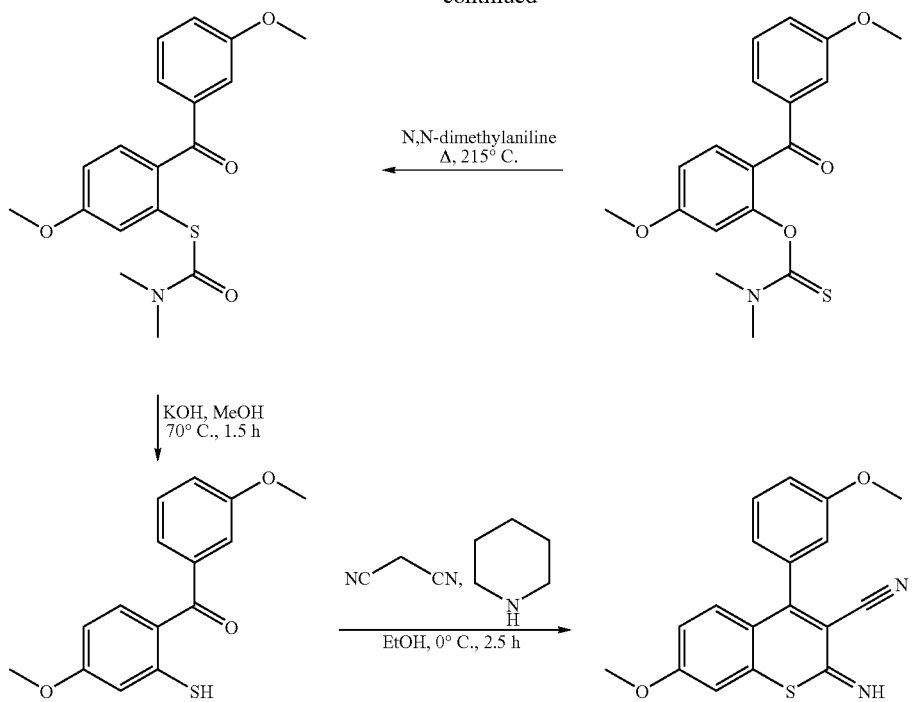

An important aspect of the present invention is the discovery that compounds having Formulae I-VI are activators of caspases and inducers of apoptosis. Therefore, these compounds are expected to be useful in a variety of clinical conditions in which there is uncontrolled cell growth and spread of abnormal cells, such as in the case of cancer.

Another important aspect of the present invention is the discovery that compounds having Formulae I-VII are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I-VII, which functions as a caspase cascade activator and inducer of apoptosis.

The present invention also includes a therapeutic method comprising administering to an animal an effective amount of a compound, or a pharmaceutically acceptable salt or prodrug of said compound of Formulae I-VII, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

In another embodiment, a pharmaceutical composition comprising a compound, or a pharmaceutically acceptable salt of said compound of Formulae I-VII, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I-VII, which functions as a caspase cascade activator and inducer of apoptosis, in combination with at least one known cancer chemotherapeutic agent, or a pharmaceutically acceptable salt of said agent. Examples of known anti-cancer agents, which can be used for combination therapy include, but not are limit to alkylating agents such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and the at least one known cancer chemotherapeutic agent are administered substantially simultaneously, i.e., the compounds are administered at the same time or one after the other, so long as the compounds reach therapeutic levels in the blood at the same time. On another embodiment, the compound of the invention and the at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of said compound of Formulae I-VII, which functions as a caspase cascade activator and inducer of apoptosis, in bioconjugation with at least one known therapeutically useful antibodies, such as Herceptin® or Rituxan®; growth factors, such as DGF, NGF; cytokines, such as IL-2, IL-4, or any molecule that binds to cell surface. The antibodies and other molecules will deliver compound of Formulae I-VII to its targets and make them effective anticancer agents. The bioconjugates also could enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of said compound of Formulae I-VII, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I-VII, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process, and one treatment strategy would be to turn on apoptosis in the lymphocytes that are causing autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, and both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model.

Therefore the application of a Fas-dependent apoptosis enhancer such as bisindolylmaleimide VIII may be therapeutically useful for the more effective elimination of detrimental cells and inhibition of T cell-mediated autoimmune diseases. Therefore an effective amount of a compound, or a pharmaceutically acceptable salt or prodrug of the compound of Formulae I-VII, which functions as a caspase cascade activator and inducer of apoptosis, is an effective treatment for autoimmune disease.

Psoriasis is a chronic skin disease that is characterized by scaly red patches. Psoralen plus ultraviolet A (PUVA) is a widely used and effective treatment for psoriasis vulgaris and Coven, et al, *Photodermatol. Photoimmunol. Photomed.* 15:22-27 (1999), reported that lymphocytes treated with psoralen 8-MOP or TMP plus UVA displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis' skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of the compound of Formulae I-VII, which functions as a caspase cascade activator and inducer of apoptosis, is an effective treatment for hyperproliferative diseases, such as psoriasis.

Synovial cell hyperplasia is a characteristic of patients with rheumatoid arthritis (RA). Excessive proliferation of RA synovial cells, as well as defective in synovial cell death might be responsible for the synovial cell hyperplasia. Wakisaka, et al., *Clin. Exp. Immunol.* 114:119-128 (1998), found that, although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells and lead to pannus formation and the destruction of joints in patients with RA. Therefore, an effective amount of a compound, or a pharmaceutically acceptable salt or prodrug of the compound of Formulae I-VII, which functions as a caspase cascade activator and inducer of apoptosis, is an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-VII, which functions as a caspase cascade activator and inducer of apoptosis, is an effective treatment for inflammation and inflammatory bowel disease.

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day of the body weight of the mammal being treated for apoptosis-mediated disorders. Preferably, approximately 0.01 to approximately 10 mg/kg is orally administered to treat or prevent such disorders. For intramuscular injection, the dose is generally approximately one-half of the oral dose. For example, a suitable intramuscular dose would be approximately 0.0025 to approximately 25 mg/kg, and most preferably, from approximately 0.01 to approximately 5 mg/kg. If a known cancer chemotherapeutic agent is also administered, it is administered in an amount with is effective to achieve its intended purpose. The amounts of such known cancer chemotherapeutic agents effective for cancer are well known to those of skill in the art.

The unit oral dose may be comprised of approximately 0.01 to approximately 50 mg, preferably approximately 0.1 to approximately 10 mg of the compound of the invention. The unit dose may be administered one or more times daily as one or more tablets, each containing from approximately 0.1 to approximately 10, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprised of excipients and auxiliaries, which facilitate processing of the compounds into preparations that can be used pharmaceutically. Preferably, the preparations, particularly those preparations which can be administered orally and which can be used for the preferred type of administration, such as tablets, dragees, and capsules; preparations which can be administered rectally, such as suppositories; as well as suitable solutions for administration by injection or orally, contain from approximately 0.01 to 99 percent (preferably from approximately 0.25 to 75 percent) of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, routes of administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resultant mixture and processing the mixture of granules, after adding suitable auxiliaries, if desired or necessary, to obtain tablets or dragee cores.

Suitable excipients are, in particular, fillers, such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG-400) or cremophor, or cyclodextrins.

Aqueous injection suspensions may contain substances, which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with a warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy, and which are obvious to those skilled in the art, are within the spirit and scope of the invention.

EXAMPLE 1

3-Cyano-7-methoxy-4-(3-bromo-4,5-dimethoxyphenyl)-2-oxo-2H-chromene

To a solution of 5-bromoveratraldehyde (1.0 g, 4.1 mmol) and ethyl cyanoacetate (0.45 mL, 4.1 mmol) in ethanol (4 mL) was added piperidine (0.4 mL, 4.1 mmol). The mixture was stirred at room temperature for 0.5 h and precipitate was collected by filtration to yield the product (1.16 g) 3-(3-bromo-4,5-dimethoxy-phenyl)-2-cyano-acrylic acid ethyl ester as a solid. To a solution of 3-methoxyphenol (0.11 mL, 1 mmol) in toluene (10 mL) was added sodium hydride (60 mg, 1.5 mmol, 60%) and the mixture was stirred at room temperature for 0.5 h. To the mixture was added 3-(3-bromo-4,5-dimethoxy-phenyl)-2-cyano-acrylic acid ethyl ester (340 mg, 1 mmol) as a solid, then the mixture was refluxed for 2 h. The solvent was evaporated and the residue was purified by chromatography on silica gel with ethyl acetate and hexane (1:2) as eluant, yielding 7 mg (1.7%) of the title compound. $^1$H NMR (CDCl$_3$): 7.34 (d, J=9.6, 1H), 7.21 (d, J=1.8, 1H), 6.98 (d, J=1.8, 1H), 6.91-6.90 (m, 2H), 3.98 (s, 3H), 3.94 (s, 3H), 3.93 (s, 3H).

EXAMPLE 2

3-Cyano-7-methoxy-4-(3,5-dimethoxyphenyl)-2-oxo-2H-chromene

The title compound was prepared from 3-methoxyphenol and 2-cyano-3-(3,5-dimethoxy-phenyl)-acrylic acid ethyl ester by a procedure similar to that described for Example 1 in 4.2% yield. $^1$H NMR (CDCl$_3$): 7.36 (d, J=9.0, 1H), 6.89-6.83 (m, 2H), 6.65-6.63 (m, 1H), 6.55-6.54 (m, 2H), 3.93 (s, 3H), 3.85 (s, 6H).

EXAMPLE 3

3-Cyano-2-imino-4-phenyl-2H-chromene

To a mixture of 2-hydroxybenzophenone (2.0 g, 10 mmol) and malononitrile (661 mg, 10 mmol) in ethanol (15 mL) was added piperidine (0.5 mL, 5.0 mmol). The mixture was stirred under 0-5° C. for 2 h. The solvent was evaporated and the residue was purified by chromatography on silica gel with ethyl acetate and hexane (1:2) as eluant, yielding 1.2 g (48%) of the title compound. $^1$H NMR (CDCl$_3$): 7.74-7.29 (m, 7H), 7.20-7.13 (m, 2H).

EXAMPLE 4

3-Cyano-4-phenyl-2-oxo-2H-chromene

To a solution of 3-cyano-2-imino-4-phenyl-2H-chromene (90 mg, 0.37 mmol) in methanol (10 mL) was added 37% HCl (0.037 ml, 0.37 mmol). The mixture was stirred at room temperature for 2 h. The solvent was evaporated and the residue was purified by chromatography on silica gel with ethyl acetate and hexane (1:2) as eluant, yielding 35 mg (39%) of the title compound. $^1$H NMR (CDCl$_3$): 7.80-7.74 (m, 1H), 7.66-7.60 (m, 3H), 7.57-7.54 (m, 1H), 7.47-7.44 (m, 2H), 7.41-7.32 (m, 2H).

EXAMPLE 5

3-Cyano-4-(3-methoxyphenyl)-2-oxo-2H-pyrrolo[2,3-h]chromene

To a solution of 3-methoxybenzaldehyde (2.0 g, 15.0 mmol) and ethyl cyanoacetate (1.56 mL, 15.0 mmol) in ethanol (10 mL) was added piperidine (0.73 ml, 7.5 mmol). The mixture was stirred at room temperature overnight. The solvent was evaporated and the crude oil was used for the next step. To a solution of 4-hydroxyindole (266.3 mg, 2 mmol) in toluene (5 mL) was added sodium hydride (100 mg, 2.5 mmol, 60%) and the mixture was stirred at room temperature for 0.5 h. To the mixture was added the 3-(3-methoxy-phenyl)-2-cyano-acrylic acid ethyl ester (462.5 mg, 2 mmol) dissolved in toluene (1 mL), then the mixture was refluxed for 2 h. The solvent was evaporated and residue was purified by chromatography on silica gel with ethyl acetate and hexane (1:2) as eluant, yielding 6 mg (0.9%) the title compound. $^1$H NMR (CDCl$_3$): 8.67 (brs, 1H), 7.54-7.48 (m, 1H), 7.35-7.31 (m, 2H), 7.15-7.01 (m, 5H), 3.88 (s, 3H).

EXAMPLE 6

3-Cyano-4-phenyl-quinolin-1H-2-one (a) N-(2-Benzoylphenyl)-2-cyano-acetamide. To a white suspension of PCl$_5$ (0.397 g, 1.90 mmol) in dichloromethane (5.8 mL) was added cyanoacetic acid (0.162 g, 1.90 mmol). The white suspension was heated at approximately 60° C. for approximately 20 min, cooled to room temperature, and 2-aminobenzophenone was added to form a yellow solution. The yellow solution was heated at reflux for approximately 30 min, cooled to approximately 0° C., diluted with water (3 mL), neutralized with 10% NaHCO$_3$ and concentrated to form a yellow precipitate. The mixture was filtered, and the solid was dried to yield 0.25 g (75%) of a yellow solid. $^1$H NMR (CDCl$_3$): 11.28 (s, 1H), 8.50 (dd, J=8.50, 1.10 Hz, 1H), 7.67 (m, 2H), 7.58 (m, 3H), 7.45 (m, 2H), 7.15 (m, 1), 3.64 (s, 2H).

(b) 3-Cyano-4-phenyl-quinolin-1H-2-one. To a yellow suspension of N-(2-benzoylphenyl)-2-cyano-acetamide (0.25 g, 0.95 mmol) in methanol (0.60 mL), cooled to approximately 0° C., was added a 25 wt % NaOMe solution in methanol (0.58 mL, 2.5 mmol). The yellow suspension was warmed to room temperature over approximately 30 min and stirred at room temperature for approximately 2 h. The reaction mixture was diluted with ethyl acetate (50 mL), washed with water (15 mL), 1 M citric acid (15 mL), 10% NaHCO$_3$ (15 mL), water (20 mL), dried over MgSO$_4$, filtered through sintered glass and concentrated to yield 0.086 g (37%) of a white solid. $^1$H NMR (DMSO-d$_6$): 12.58 (s, 1H), 7.65 (m, 4H), 7.47 (m, 3H), 7.21 (m, 2H).

EXAMPLE 7

3-Cyano-7-methoxy-4-(3-methoxy-phenyl)-quinolin-1H-2-one (a) N-(3-Methoxyphenyl)-acetamide. A brown solution of m-anisidine (10.00 g, 81.17 mmol), 1,4-dioxane (162 mL), and acetic anhydride (11.49 mL, 121.8 mmol) was refluxed for 2 h. The solution was cooled to room temperature, concentrated by rotary evaporation to remove approximately 50 mL of 1,4-dioxane, diluted with water (25 mL) and cooled to 0° C. The resultant precipitate was filtered through sintered glass yielding 10.18 g (75%) of a pink solid. $^1$H NMR (CDCl$_3$): 7.47 (s, 1H), 7.26 (m, 1H), 7.20 (t, J=8.42, 8.10 Hz, 1H), 6.97 (dd, J=8.10, 0.89 Hz, 1H), 6.65 (dd, J=8.42, 2.10 Hz, 1H), 3.79 (s, 3H), 2.16 (s, 3H).

(b) N-[5-Methoxy-2-(3-methoxybenzoyl)-phenyl]-acetamide. To a yellow solution of N-(3-methoxy-phenyl)-acetamide (1.00 g, 6.05 mmol) in dichloromethane (15.1 mL), cooled to approximately 0° C., was added anisoyl chloride (1.02 mL, 7.26 mmol) and aluminum chloride (1.77 g, 13.3 mmol). The resultant brown mixture was heated under reflux for approximately 3 h, cooled to approximately 0° C., quenched by the slow addition of water (15 mL) and diluted with dichloromethane (100 mL). The organic layer was washed with water (25 mL), 10% Na$_2$CO$_3$ (2×25 mL), water (25 mL), dried over MgSO$_4$, filtered through sintered glass and concentrated to yield approximately 2 g of a yellow residual oil. The residue was purified by column chromatography (elution with EtOAC:hexanes, 1:3) to yield 0.15 g (8%) of the title compound as a white solid. $^1$H NMR (CDCl$_3$): 11.56 (s, 1H), 8.37 (d, J=2.75 Hz, 1H), 7.54 (d, J=8.71 Hz, 1H), 7.38 (t, J=8.10, 6.97 Hz, 1H), 7.14 (m, 3H), 6.57 (dd, J=9.31, 2.47 Hz, 1H), 3.90 (s, 3H), 3.85 (s, 3H), 2.26 (s, 3H).

(c) (2-Amino-4-methoxyphenyl)-(3-methoxy-phenyl)-methanone. To a yellow solution of N-[5-methoxy-2-(3-methoxybenzoyl)-phenyl]-acetamide (0.150 g, 0.500 mmol) in ethanol (5.0 mL) was added concentrated HCl (1.00 mL). The yellow solution was heated under reflux for approximately 23 h, cooled to room temperature, diluted with ethanol (5 mL) and neutralized with 1 M NaOH. The aqueous layer was extracted with EtOAc (2×50 mL), dried over MgSO$_4$, filtered through sintered glass and concentrated to yield 0.123 g (95%) of a yellow oil. $^1$H NMR (CDCl$_3$): 7.36 (m, J=8.24, 7.42, 1.92, 0.83 Hz, 2H), 7.13 (m, J=7.96, 7.41, 1.92, 0.55 Hz, 2H), 7.02 (m, J=8.24, 7.97, 7.42, 1.92, 0.55 Hz, 1H), 6.38 (brs, 2H), 6.16 (m, J=8.24, 7.42, 0.83, 0.55 Hz, 2H), 3.83 (s, 3H), 3.79 (s, 3H).

(d) 2-Cyano-N-[5-methoxy-2-(3-methoxybenzoyl)-phenyl]-acetamide. The title compound was prepared from (2-amino-4-methoxy-phenyl)-(3-methoxy-phenyl)-methanone and cyanoacetic acid by a procedure similar to Example 6a in 97% yield. $^1$H NMR (CDCl$_3$): 12.16 (s, 1H), 8.27 (d, J=2.47 Hz, 1H), 7.61 (d, J=8.79 Hz, 1H), 7.38 (t, J=7.97, 4.95 Hz, 1H), 7.15 (m, 3H), 6.65 (dd, J=8.79, 2.47 Hz, 1H), 3.91 (s, 3H), 3.85 (s, 3H), 3.65 (s, 2H).

(e) 3-Cyano-7-methoxy-4-(3-methoxyphenyl)-quinolin-1H-2-one. The title compound was prepared from 2-cyano-N-[5-methoxy-2-(3-methoxy-benzoyl)-phenyl]-acetamide and NaOMe by a procedure similar to Example 6b in 41% yield. $^1$H NMR (CDCl$_3$): 12.80 (brs, 1H), 7.48 (t, J=8.01 Hz, 1H), 7.33 (d, J=9.10 Hz, 1H), 7.10 (dd, J=8.52, 2.53 Hz, 1H), 7.03 (m, 1H), 6.96 (m, 2H), 6.80 (dd, J=9.10, 2.10 Hz, 1H), 3.97 (s, 3H), 3.88 (s, 3H).

EXAMPLE 8

7-Chloro-3-cyano-4-(3-methoxy-phenyl)-quinolin-1H-2-one (a) (2-Amino-4-chlorophenyl)-(3-methoxyphenyl)-methanone. To a yellow solution of 2-amino-4-chloro-N-methoxy-N-methylbenzamide (0.423 g, 1.97 mmol) and 3-bromoanisole (0.25 mL, 1.97 mmol) in THF (9.9 mL), cooled to approximately −78° C. was added n-butyllithium (2.5 M solution in hexanes, 1.58 mL, 3.94 mmol) dropwise over approximately 2 min. The dark brown solution was stirred for 30 min, while being cooled to approximately 78° C. The mixture was warmed to room temperature and quenched with 1N HCl (3 mL). The reaction mixture was then extracted with EtOAc (50 mL), washed with water (2×20 mL), dried over MgSO$_4$, filtered through sintered glass and concentrated to yield 0.55 g of a brown oil. The oil was purified by column chromatography (elution with EtOAc:hexanes, 1:1) to yield 0.294 g (57%) of the title compound as a white solid. $^1$H NMR (CDCl$_3$): 7.35 (m, J=8.79, 8.24, 1.10, 0.55 Hz, 2H), 7.14 (m, 2H), 7.05 (m, J=8.24, 2.47 Hz, 1H), 6.69 (dd, J=2.20, 1.92, 0.83, 0.55 Hz, 1H), 6.52 (m, J=8.79, 2.20, 1.92, 1.10, 0.82 Hz, 1H), 6.27 (brs, 2H), 3.81 (s, 3H).

(b) 2-Cyano-N-[5-chloro-2-(3-methoxybenzoyl)-phenyl]-acetamide. The title compound was prepared from (2-amino-4-chloro-phenyl)-(3-methoxyphenyl)-methanone and cyanoacetic acid by a procedure similar to Example 6a in 88% yield. $^1$H NMR (CDCl$_3$): 11.46 (s, 1H), 8.60 (d, J=1.92 Hz, 1H), 7.55 (d, J=8.52 Hz, 1H), 7.38 (t, J=8.52, 7.69 Hz, 1H), 7.15 (m, J=7.69, 1.92, 4H), 3.84 (s, 3H), 3.67 (s, 2H).

(c) 7-Chloro-3-cyano-4-(3-methoxyphenyl)-quinolin-1H-2-one. The title compound was prepared from 2-cyano-N-[5-chloro-2-(3-methoxy-benzoyl)-phenyl]-acetamide and NaOMe by a procedure similar to Example 6b in 45% yield. $^1$H NMR (CDCl$_3$): 12.50 (brs, 1H), 7.55 (d, J=1.92 Hz, 1H), 7.50 (dd, J=8.24 Hz, 1H), 7.40 (d, J=8.79 Hz, 1H), 7.20 (m, J=9.07, 8.79, 2.20, 1.92 Hz, 1H), 7.13 (m, J=7.69, 7.41, 2.75, 2.47 Hz, 1H), 7.02 (m, J=8.24 Hz, 1H), 6.97 (m, J=8.24 Hz, 1H), 3.89 (s, 3H).

EXAMPLE 9

4-(3-Bromo-4,5-dimethoxy-phenyl)-3-cyano-7-methoxy-quinolin-1H-2-one (a) N-[2-(3-Bromo-4,5-dimethoxybenzoyl)-5-methoxyphenyl]-acetamide. The title compound was prepared from m-acetanisidine, 3-bromo-4,5-dimethoxy benzoyl chloride and AlCl$_3$ by a procedure similar to Example 7b in 8% yield. $^1$H NMR (CDCl$_3$): 11.33 (s, 1H), 8.37 (d, J=2.47 Hz, 1H), 7.54 (d, J=8.79 Hz, 1H), 7.40 (d, J=1.92 Hz, 1H), 7.17 (d, J=1.92 Hz, 1H), 6.62 (dd, J=8.79, 2.47 Hz, 1H), 3.94 (s, 3H), 3.92 (s, 3H), 3.90 (s, 3H), 2.50 (s, 3H).

(b) (2-Amino-4-methoxy-phenyl)-(3-bromo-4,5-dimethoxy-phenyl)-methanone. The title compound. was prepared from N-[2-(3-bromo-4,5-dimethoxybenzoyl)-5-methoxyphenyl]-acetamide and HCl by a procedure similar to Example 7c in 28% yield. $^1$H NMR (CDCl$_3$): 7.41 (d, J=9.00 Hz, 1H), 7.35 (d, J=2.10 Hz, 1H), 7.13 (d, J=1.80 Hz, 1H), 6.29 (brs, 2H), 6.21 (dd, J=9.00, 2.70 Hz, 1H), 6.16 (d, J=2.70 Hz, 1H), 3.91 (s, 3H), 3.89 (s, 3H), 3.84 (s, 3H).

(c) N-[2-(3-Bromo-4,5-dimethoxybenzoyl)-5-methoxyphenyl]-2-cyano-acetamide.

The title compound was prepared from (2-amino-4-methoxyphenyl)-(3-bromo-4,5-dimethoxyphenyl)-methanone and cyano-acetic acid by a procedure similar to Example 6a in 60% yield. $^1$H NMR (CDCl$_3$): 11.96 (s, 1H), 8.26 (d, J=2.48 Hz, 1H), 7.61 (d, J=9.07 Hz, 1H), 7.40 (d, J=1.93 Hz, 1H), 7.20 (d, J=1.93 Hz, 1H), 6.70 (dd, J=9.07, 2.47 Hz, 1H), 3.95 (s, 3H), 3.92 (s, 3H), 3.91 (s, 3H), 3.61 (s, 2H).

(d) 4-(3-Bromo-4,5-dimethoxyphenyl)-3-cyano-7-methoxy-quinolin-1H-2-one. The title compound was prepared from N-[2-(3-bromo-4,5-dimethoxybenzoyl)-5-methoxyphenyl]-2-cyano-acetamide and NaOMe by a procedure similar to Example 6b in 33% yield. $^1$H NMR (CDCl$_3$): 11.90 (s, 1H), 7.35 (d, J=9.0 Hz, 1H), 7.20 (d, J=1.80 Hz, 1H), 6.94 (dd, J=9.00, 1.80 Hz, 2H), 6.85 (dd, J=8.24 Hz, 1H), 3.98 (s, 3H), 3.97 (s, 3H), 3.92 (s, 3H).

EXAMPLE 10

3-Cyano-2-imino-4-(5-methyl-pyridin-3-yl)-2H-pyrrolo[2,3-h]chromene

To a suspension of 2-amino-3-cyano-4-(5-methyl-pyridin-3-yl)-4H-pyrrolo[2,3-h]chromene (80 mg, 0.27 mmol), and molecular sieves (160 mg) in CH$_2$Cl$_2$ (10 mL) was added 2,3-dichloro-5,6-dicyano-1,4-benzoquinone (66 mg, 0.29 mmol). The reaction mixture turned brown in color. The mixture was stirred at room temperature for approximately 1.5 h. The reaction mixture was diluted with EtOAc (50 mL), washed with saturated NaHCO$_3$ (2×12 mL), brine (10 mL), dried over MgSO$_4$, and evaporated to yield a yellow solid (86 mg). $^1$H NMR (DMSO-d$_6$): 11.83 (s, 1H), 8.70 (s, 1H), 8.65 (d, J=1.2 Hz, 1H), 8.54 (d, J=2.1 Hz, 1H), 7.84 (m, 1H), 7.52 (t, J=3.0 Hz, 1H), 7.25 (dd, J=0.9, 9.0 Hz, 1H), 6.71 (m, 1H), 6.76 (d, J=8.4 Hz, 1H), 2.43 (d, J=0.6 Hz, 3H).

EXAMPLE 11

3-Cyano-2-imino-7-methyl-4-(5-methyl-pyridin-3-yl)-2H-pyrrolo[2,3-h]chromene

The title compound was prepared from 2-amino-3-cyano-7-methyl-4-(5-methyl-pyridin-3-yl)-4H-pyrrolo[2,3-h] chromene by a procedure similar to that described for Example 10. $^1$H NMR (DMSO-d$_6$): 8.73 (s, 1H), 8.66 (d, J=1.8 Hz, 1H), 8.55 (d, J=2.1 Hz, 1H), 7.84 (m, 1H), 7.51 (d, J=3.3 Hz, 1H), 7.31 (d, J=9.0 Hz, 1H), 6.73-6.70 (m, 2H), 3.82 (s, 3H), 2.43 (s, 3H).

EXAMPLE 12

4-(3-Bromo-4,5-dimethoxy-phenyl)-3-cyano-2-imino-7-methyl-2H-pyrrolo[2,3-h]chromene The title compound was prepared from 2-amino-4-(3-bromo-4,5-dimethoxy-phenyl)-3-cyano-7-methyl-4H-pyrrolo[2,3-h]chromene by a procedure similar to that described for Example 10. $^1$H NMR (CDCl$_3$): 7.23 (d; J=2.1 Hz, 1H), 7.12 (d, J=3.3 Hz, 1H), 7.07 (dd, J=0.6, 9.0 Hz, 1H), 6.98 (s, 1H), 6.98-6.95 (m, 2H), 6.87 (d, J=3.0 Hz, 1H), 3.97 (s, 3H), 3.92 (s, 3H), 3.83 (s, 3H), 1.64 (brs, 1H).

EXAMPLE 13

3-Cyano-4-(5-methyl-pyridin-3-yl)-2-oxo-2H-pyrrolo[2,3-h]chromene

A solution of 3-cyano-2-imino-4-(5-methyl-pyridin-3-yl)-2H-pyrrolo[2,3-h]chromene (83 mg, 0.28 mmol) in 10% HCl (5 mL) was stirred at room temperature for approximately 5 h. The yellow suspension was diluted with water (5 mL), neutralized to approximate pH=10 using 10% NaOH and extracted with EtOAc (3×25 mL). The EtOAc extracts were washed with brine (10 mL), dried over MgSO$_4$, and evaporated to yield a yellow solid. The solid was purified by flash column chromatography (silica gel, EtOAc:hexanes, 50-80% EtOAc) to yield a yellow solid (27 mg, 35%). $^1$H NMR (DMSO-d$_6$): 12.10 (s, 1H), 8.70 (d, J=1.8 Hz, 1H), 8.58 (d, J=2.1 Hz, 1H), 7.88 (m, 1H), 7.62 (d, J=3.3 Hz, 1H), 7.45 (dd, J=0.3, 9.0 Hz, 1H), 6.91-6.88 (m, 2H), 2.45 (s, 3H).

EXAMPLE 14

3-Cyano-4-(5-methyl-pyridin-3-yl)-7-methyl-2-oxo-2H-pyrrolo[2,3-h]chromene

A solution of 3-cyano-2-imino-4-(5-methyl-pyridin-3-yl)-7-methyl-2H-pyrrolo[2,3-h]chromene (50 mg, 0.14 mmol) in 10% HCl (2 mL) and DMSO (0.5 mL) was stirred at room temperature for approximately 4 h. The yellow suspension was diluted with water (5 mL), neutralized to approximate pH=9 using 10% NaOH, and extracted with EtOAc (3×20 mL). The EtOAc extracts were washed with brine (10 mL), dried over MgSO$_4$, and evaporated to yield a yellow solid. The solid was purified by flash column chromatography (silica gel, EtOAc:hexanes, 50-80% EtOAc) to yield a yellow solid (31 mg, 68%). $^1$H NMR (DMSO-d$_6$): 8.71 (d, J=1.8 Hz, 1H), 8.58 (d, J=2.1 Hz, 1H), 7.88 (m, 1H), 7.61 (d, J=3.0Hz, 1H), 7.53 (d, J=8.7 Hz, 1H), 6.93 (d, J=8.7 Hz, 1H), 6.91 (d, J=3.3 Hz, 1H), 3.88 (s, 3H), 2.45 (s, 3H).

EXAMPLE 15

4-(3-Bromo-4,5-dimethoxy-phenyl)-3-cyano-7-methyl-2-oxo-2H-pyrrolo[2,3-h]chromene To a solution of 4-(3-bromo-4,5-dimethoxy-phenyl)-3-cyano-2-imino-7-methyl-2H-pyrrolo[2,3-h]chromene (100 mg, 0.216 mmol) in THF:water (10:2) was added a ZnCl$_2$ solution (1 mL, 1.0 M in CH$_2$Cl$_2$). The solution was stirred at room temperature for approximately 7 h. The reaction mixture was made basic with saturated NaHCO$_3$ (10 mL), and extracted with EtOAc (2×25 mL). The EtOAc extracts were washed with brine (10 mL), dried over MgSO$_4$, and evaporated to yield a yellow solid. The solid was purified by flash column chromatography (silica gel, EtOAc:hexanes 30-70% EtOAc) to yield 17 mg (18%) of the product as a yellow solid. $^1$H NMR (acetone-d$_6$): 7.51-7.48 (m, 2H), 7.42 (d, J=1.8 Hz, 1H), 7.34 (d, J=2.1 Hz, 1H), 7.17 (d, J=8.7 Hz, 1H), 6.91 (dd, J=0.6, 3.3 Hz, 2H), 3.98 (s, 3H), 3.97 (s, 3H), 3.85 (s, 3H).

EXAMPLE 16

4-(3,5-Dimethoxyphenyl)-3-cyano-2-oxo-2H-pyrrolo[2,3-h]chromene

To a solution of 3,5-dimethoxybenzaldehyde (1.35 g, 8.12 mmol) and ethyl cyanoacetate (0.92 ml, 8.1 mmol) in ethanol (10 mL) was added piperidine (0.4 mL, 4 mmol). The mixture was stirred at room temperature for approximately 2 h. A precipitate formed, which was collected by filtration and dried to yield approximately 2.12 g of a white solid, which was used directly in the next step. To a solution of 4-hydroxyindole (250 mg, 1.91 mmol) in THF (10 mL) was added sodium hydride (153 mg, 3.80 mmol, 60%) and the mixture was stirred at room temperature for approximately 10 min. To the mixture was added a solution of 3-(3,5-dimethoxyphenyl)-2-cyano-acrylic acid ethyl ester (500 mg, 1.91 mmol, prepared as described above) in THF (2 mL). The mixture was heated at approximately 60° C. overnight. The solvent was evaporated and the residue was purified by flash column chromatography (silica gel, EtOAc: hexane, 1:2), yielding 7 mg (1.1%) of the title compound. $^1$H NMR (CDCl$_3$): 8.64 (brs, 1H), 7.35-7.24 (m, 2H), 7.19-7.16 (m, 1H), 7.04 (s, 1H), 6.65-6.59 (m, 3H), 3.85 (s, 6H).

EXAMPLE 17

3-Cyano-4-(3-methoxy-phenyl)-7-methoxy-2-oxo-2H-chromene

The title compound was prepared from 3-methoxyphenol and 3-(3-methoxyphenyl)-2-cyano-acrylic acid ethyl ester by a procedure similar to that described for Example 16 in 0.2% yield. $^1$H NMR (CDCl$_3$): 7.50 (t, J=8.1 Hz, 1H), 7.32 (d, J=8.7 Hz, 1H), 7.12 (dd, J=8.4, 2.4 Hz, 1H), 7.03-6.96 (m, 2H), 6.90-6.83 (m, 2H), 3.93 (s, 3H), 3.87 (s, 3H).

EXAMPLE 18

7-Amino-4-(3-bromo-4,5-dimethoxyphenyl)-3-cyano-2-oxo-2H-chromene

The title compound was prepared from 3-aminophenol and 3-(3-bromo-4,5-dimethoxyphenyl)-2-cyano-acrylic acid ethyl ester by a procedure similar to that described for Example 16 in 7% yield. $^1$H NMR (CDCl$_3$): 7.20-7.16 (m, 2H), 6.96 (d, J=2.1 Hz, 1H), 6.59-6.55 (m, 2H), 4.63 (brs, 2H), 3.96 (s, 3H), 3.92 (s, 3H).

EXAMPLE 19

2-Amino-4-(3-bromo-4,5-dimethoxyphenyl)-3-cyano-5,6-dihydro-benzo[h]quinoline a) 2-(3-Bromo-4,5-dimethoxy-benzylidene)-3,4-dihydro-2H-naphthalen-1-one: To a solution of 5-bromoveratraldehyde (245 mg, 1 mmol) and alpha-tetralone (146 mg, 1 mmol) in ethanol (10 mL) was added NaOH (40 mg, 1 mmol) and the mixture was stirred at room temperature overnight. The solution was neutralized with saturated aqueous NH$_4$Cl and the solvent was removed under vacuum. The crude material was purified by column chromatography (silica gel, EtOAc:hexanes, 1:2), to yield 300 mg (80%) of the title compound. $^1$H NMR (CDCl$_3$): 8.13 (d, J=7.5 Hz, 1H), 7.74 (s, 1H), 7.54-7.48 (m, 1H), 7.38 (t, J=7.5 Hz, 1H), 7.28-7.24 (m, 2H), 6.91 (d, J=1.8 Hz, 1H), 3.91-3.90 (m, 6H), 3.15-3.11 (m, 2H), 2.97 (t, J=6.9 Hz, 2H).

b) 2-Amino-4-(3-bromo-4,5-dimethoxyphenyl)-3-cyano-5,6-dihydro-benzo[h]quinoline: To a solution of 2-(3-bromo-4,5-dimethoxy-benzylidene)-3,4-dihydro-2H-naphthalen-1-one (300 mg, 0.8 mmol) in ethanol (10 mL) was added cyanothioacetamide (80 mg, 0.8 mmol) and NH$_4$Ac (62 mg, 0.8 mmol) and the mixture was stirred under reflux for approximately 2 h. The solvent was removed under vacuum. The crude material was purified by column chromatography (silica gel, EtOAc:hexane, 1:3) to yield 6 mg (2%) of the title compound. $^1$H NMR (CDCl$_3$): 8.27-8.24 (m, 1H), 7.38-7.35 (m, 2H), 7.23-7.20 (m, 1H), 7.09 (d, J=1.8 Hz, 1H), 6.83 (d, J=1.8 Hz, 1H), 5.19 (brs, 2H), 3.94 (s, 3H), 3.90 (s, 3H), 2.82-2.69 (m, 2H), 2.64-2.62 (m, 2H).

EXAMPLE 20

4-(3-Bromo-4,5-dimethoxyphenyl)-3-cyano-7,8-dihydro-8,8-dimethyl-2-oxo-2H-furo[3,2-h]chromene The title compound was prepared from 2,3-dihydro-2,2-dimethylbenzofuran-7-ol and 3-(3-bromo-4,5-dimethoxyphenyl)-2-cyano-acrylic acid ethyl ester by a procedure similar to that described for Example 16 in 0.7% yield. $^1$H NMR (CDCl$_3$): 7.51-7.50 (m, 1H), 7.31-7.30 (m, 1H), 7.07 (dd, J=1.2, 8.1 Hz, 1H), 6.80 (d, J=8.4 Hz, 1H), 3.94-3.91 (m, 6H), 3.34 (s, 2H), 1.52 (s, 6H).

EXAMPLE 21

3-Cyano-7-dimethylamino-4-(3-bromo-4,5-dimethoxyphenyl)-2-oxo-2H-chromene

The title compound was prepared from 3-dimethylaminophenol and 3-(3-bromo-4,5-dimethoxyphenyl)-2-cyano-acrylic acid ethyl ester by a procedure similar to that described for Example 16 in 0.5% yield. $^1$H NMR (CDCl$_3$): 7.21-7.18 (m, 2H), 6.98 (d, J=1.8 Hz, 1H), 6.62 (dd, J=2.4, 9 Hz, 1H), 6.53 (d, J=2.7 Hz, 1H), 3.96 (s, 3H), 3.92 (s, 3H), 3.15 (s, 6H).

EXAMPLE 22

7-Amino-3-cyano-4-(3,5-dimethoxyphenyl)-2-oxo-2H-chromene

The title compound was prepared from 3-aminophenol and 3-(3,5-dimethoxyphenyl)-2-cyano-acrylic acid ethyl ester by a procedure similar to that described for Example 16 in 0.5% yield. $^1$H NMR (CDCl$_3$): 7.42 (d, J=8.4 Hz, 1H), 6.72 (d, J=2.4 Hz, 2H), 6.61-6.60 (m, 1H), 6.20 (d, J=2.1 Hz, 1H), 6.10 (dd, J=2.1, 8.7 Hz, 1H), 4.30 (brs, 2H), 3.83 (s, 6H).

EXAMPLE 23

3-Cyano-7-dimethylamino-4-(3,5-dimethoxyphenyl)-2-oxo-2H-chromene

The title compound was prepared from 3-dimethylaminophenol and 3-(3,5-dimethoxyphenyl)-2-cyano-acrylic acid ethyl ester by a procedure similar to that described for Example 16 in 0.4% yield. $^1$H NMR (DMSO-d$_6$): 7.09 (d, J=8.7 Hz, 1H), 6.80 (d, J=7.5 Hz, 1H), 6.73-6.71 (m, 2H), 6.65 (d, J=2.1 Hz, 2H), 3.80 (s, 6H), 3.11 (s, 6H).

EXAMPLE 24

3-Cyano-4-(2,5-dimethoxyphenyl)-2-oxo-2H-pyrrolo[2,3-h]chromene

The title compound was prepared from 4-hydroxyindole and 3-(2,5-dimethoxyphenyl)-2-cyano-acrylic acid ethyl ester by a procedure similar to that described for Example 16 in 2.6% yield. $^1$H NMR (CDCl$_3$): 8.64 (s, 1H), 7.33-7.31 (m, 1H), 7.29-7.24 (m, 1H), 7.10-7.01 (m, 4H), 6.83-6.82 (m, 1H), 3.82 (s, 3H), 3.77 (s, 3H).

EXAMPLE 25

4-(3-Bromo-4,5-dimethoxy-phenyl)-3-cyano-7-methylamino-2-oxo-2H-chromene

To a flask containing anhydrous DMF (0.5 mL), heated to approximately 65° C., was added tert-butylnitrite (0.40 mL, 3.0 mmol) followed by 2-amino-4-(3-bromo-4,5-dimethoxy-phenyl)-3-cyano-7-dimethyl-amino-4H-chromene (52 mg, 0.12 mmol) in anhydrous DMF (0.5 mL). The reaction mixture was stirred at approximately 65° C. for approximately 15 min, and FeSO$_4$-7H$_2$O (92 mg, 0.33 mmol) was added in one portion. The reaction mixture was stirred for approximately 30 min, cooled to room temperature, diluted with EtOAc (25 mL), washed with water (10 mL), brine (10 mL), dried over MgSO$_4$ and evaporated to yield a yellow solid. The crude solid was purified by column chromatography (silica gel, EtOAc:hexanes 1:2 to 1:1) to yield 8 mg (16%) of the product as a yellow solid. $^1$H NMR (CDCl$_3$): 7.73 (dd, J=2.4, 9.3 Hz, 1H), 7.59 (d, J=2.4 Hz, 1H), 7.56 (d, J=9.0 Hz, 1H), 7.26 (s, 1H), 7.03 (d, J=1.8 Hz, 1H), 4.00 (s, 3H), 3.95 (s, 3H), 3.46 (s, 3H).

EXAMPLE 26

7-Amino-4-(3-bromo-4,5-dimethoxy-phenyl)-3-cyano-2-imino-2H-chromene

The title compound was prepared from 4-(3-bromo-4,5-dimethoxy-phenyl)-3-cyano-2,7-diamino-2H-chromene by a procedure similar to that described for Example 10. $^1$H NMR (DMSO-d$_6$): 8.36 (brs, 1H), 7.28 (dd, J=2.4, 9.3 Hz, 1H), 7.20 (d, J=1.8 Hz, 1H), 6.79 (d, J=8.7 Hz, 1H), 6.63 (brs, 2H), 6.41 (dd, J=1.8, 8.4 Hz, 1H), 6.33 (d, J=2.1 Hz, 1H), 3.86 (s, 3H), 3.83 (d, J=0.3 Hz, 3H).

EXAMPLE 27

7-Bromo-4-(3-bromo-4,5-dimethoxy-phenyl)-3-cyano-2-imino-2H-chromene

To a suspension of tert-butylnitrite (34 mg, 0.33 mmol) and CuBr$_2$ (68 mg, 0.30 mmol) in anhydrous acetonitrile (1.5 mL), cooled to approximately 0° C., was added 7-amino-3-cyano-2-imino-4-(3-bromo-4,5-dimethoxy-phenyl)-2H-chromene (100 mg, 0.25 mmol). The reaction mixture was stirred at approximately 0° C. for approximately 4 h, diluted with EtOAc (50 mL), washed with saturated NaHCO$_3$ (25 mL) and brine (10 mL), dried over MgSO$_4$, and evaporated to yield a yellow solid. The solid was purified by column chromatography (silica gel, EtOAc:hexanes, 1:2 to 1:1) to yield 50 mg (43%) of the title compound as a yellow solid. $^1$H NMR (CDCl$_3$): 7.82 (brs, 1H), 7.38 (m, 1H), 7.30 (dd, J=2.1, 8.7 Hz, 1H), 7.18 (d, J=2.1 Hz, 1H), 7.09 (d, J=9.0 Hz, 1H), 6.93 (m, 1H), 3.96 (s, 3H), 3.92 (s, 3H).

EXAMPLE 28

4-(3-Bromo-4,5-dimethoxy-phenyl)-7-chloro-3-cyano-2-oxo-2H-chromene

To a suspension of 7-amino-4-(3-bromo-4,5-dimethoxy-phenyl)-3-cyano-2-imino-2H-chromene (99 mg, 0.25 mmol) in anhydrous THF (10 mL), cooled to approximately 0° C., was added tert-butylnitrite (0.10 mL, 0.66 mmol), followed by CuCl$_2$ (104 mg, 0.774 mmol). The reaction mixture was stirred at approximately 0° C. for approximately 3 h and the solvent was evaporated. The residue was suspended in anhydrous acetonitrile (5 mL) and CuCl$_2$ (104 mg, 0.776 mmol) was added to the reaction mixture, while stirring at approximately 0° C. The mixture was allowed to gradually warm and stirred at room temperature for approximately 17 h and the solvent was evaporated and the residue was diluted with EtOAc (50 mL). The EtOAc solution was washed with saturated NaHCO$_3$ (15 mL) and brine (10 mL), dried over MgSO$_4$ and evaporated. The residue was purified by column chromatography (silica gel, EtOAc:hexanes, 1:4) to yield 66 mg (63%) of the title compound as a yellow solid. $^1$H NMR (CDCl$_3$): 7.48 (d, J=1.8 Hz, 1H), 7.40 (d, J=8.4 Hz, 1H), 7.33 (dd, J=1.8, 8.4 Hz, 1H), 7.22 (d, J=2.1 Hz, 1H), 6.98 (d, J=2.1 Hz, 1H), 3.99 (s, 3H), 3.93 (s, 3H).

EXAMPLE 29

4-(3-Bromo-4,5-dimethoxy-phenyl)-7-chloro-3-cyano-2-imino-2H-chromene

To a suspension of 7-amino-4-(3-bromo-4,5-dimethoxy-phenyl)-3-cyano-2-imino-2H-chromene (82 mg, 0.20 mmol) in anhydrous acetonitrile (10 mL), cooled to approximately 0° C., was added tert-butylnitrite (0.8 mL, 6 mmol), followed by CuCl$_2$ (104 mg, 0.774 mmol). The reaction mixture was stirred at approximately 0° C. for approximately 4 h, diluted with EtOAc (50 mL), washed with saturated NaHCO$_3$ (25 mL) and brine (15 mL), dried over MgSO$_4$, and evaporated to yield a yellow solid. The crude solid was purified by column chromatography (silica gel, EtOAc:hexanes, 1:3) to yield the title compound as a yellow solid: $^1$H NMR (CDCl$_3$) 7.82 (s, 1H), 7.22-7.16 (m, 4H), 6.94 (d, J=1.8 Hz, 1H), 3.96 (s, 3H), 3.92 (s, 3H).

EXAMPLE 30

2-Imino-3-cyano-7-methoxy-4-(3'-methoxy-phenyl)-2H-thiochromene (a) 2-hydroxy-4-methoxyphenyl-(3'-methoxyphenyl)-methanone: To a solution of 3-methoxyphenol (500 μL, 4.55 mmol) in 5 mL of anhydrous toluene was added meta-anisoyl chloride (640 μL, 4.55 mmol) at approximately 0° C. followed by boron trichloride (4.55 mL of a 1.0 M solution in xylene, 4.55 mmol). The resultant mixture was warmed and stirred at approximately 85° C. for 24 h. It was then diluted with 40 mL of ether, washed twice with 25 mL portions of saturated aqueous sodium bicarbonate, dried with sodium sulfate, concentrated and purified by flash column chromatography (silica gel, EtOAc:hexanes, 1:5) to yield 883 mg of the title compound as a colorless oil. $^1$H NMR (CDCl$_3$): 7.53 (d, J=8.9 Hz, 1H), 7.39 (dd, J=7.5, 0.5 Hz, 1H), 7.18-7.20 (m, 1H), 7.15-7.16 (m, 1H), 7.10 (ddd, J=8.3, 2.6, 1.0 Hz, 1H), 6.52 (d, J=2.5 Hz, 1H), 6.41 (dd, J=9.0, 2.6 Hz, 1H), 3.87 (s, 3H), 3.86 (s, 3H).

(b) Dimethylthiocarbamic Acid O-[5-methoxy-2-(3'-methoxybenzoyl)-phenyl]ester: A mixture of (2-hydroxy-4-methoxy-phenyl)-(3'-methoxy-phenyl)-methanone (872 mg, 3.38 mmol), dimethylthiocarbamoyl chloride (835 mg, 6.76 mmol) and 1,4-diazabicyclo[2.2.2]octane (758 mg, 6.76 mmol) in 10 mL of anhydrous DMF was stirred overnight at room temperature. A portion of 100 mL of ether was added and the resultant mixture was washed twice with a saturated solution of aqueous sodium bicarbonate, dried with sodium sulfate and concentrated. Purification by flash column chromatography (silica gel, EtOAc:hexanes, 15% to 20% EtOAc) yielded 975 mg (83%) of dimethylthiocarbamic acid O-[5-methoxy-2-(3'-methoxybenzoyl)-phenyl]ester as a pale yellow oil. $^1$H NMR (CDCl$_3$): 7.51 (d, J=8.6 Hz, 1H), 7.33-7.35 (m, 2H), 7.08-7.11 (m, 1H), 6.83 (dd, J=8.6, 2.5 Hz, 1H), 6.41 (d, J=2.4 Hz, 1H), 3.90 (s, 3H), 3.85 (s, 3H), 3.32 (s, 3H), 3.16 (s, 3H).

(c) Dimethylthiocarbamic Acid S-[5-methoxy-2-(3'-methoxy-benzoyl)-phenyl]ester: Dimethylthiocarbamic acid O-[5-methoxy-2-(3'-methoxybenzoyl)-phenyl]ester (879 mg, 2.54 mmol) was stirred in 8 mL of N,N-dimethylaniline at approximately 215° C. for approximately 3 h. After cooling at room temperature, a portion of 100 mL of ether was added. The resultant mixture was washed twice with a solution of approximately 10% hydrochloric acid, once with a saturated aqueous solution of sodium bicarbonate, dried with sodium sulfate and concentrated. The crude compound was purified by flash column chromatography (silica gel, EtOAc:hexanes 1:5) to yield 502 mg (57%) of dimethylthiocarbamic acid S-[5-methoxy-2-(3'-methoxy-benzoyl)-phenyl]ester as a pale yellow oil. $^1$H NMR (CDCl$_3$): 7.40 (d, J=8.5 Hz, 1H), 7.30-7.34 (m, 2H), 7.19 (d, J=2.6 Hz, 1H), 7.07-7.10 (m, 1H), 6.95-6.97 (m, 1H), 3.88 (s, 3H), 3.82 (s, 3H), 2.89 (s, 6H).

(d) 2-Mercapto-4-methoxy-phenyl)-(3'-methoxy-phenyl)-methanone: A mixture of dimethylthiocarbamic acid S-[5-methoxy-2-(3'-methoxybenzoyl)-phenyl]ester (164 mg, 0.475 mmol) and potassium hydroxide (200 mg, 3.56 mmol) was stirred in approximately 2 mL of dry methanol at approximately 70° C. for approximately 1.5 h. After cooling at room temperature, the solvent was removed. The crude compound obtained was purified by column chromatography (silica gel, EtOAc:hexanes, 1:5) to yield 35 mg (27%) of (2-mercapto-4-methoxyphenyl)-(3'-methoxyphenyl)-methanone as a pale yellow oil. $^1$H NMR (CDCl$_3$): 7.50 (d, J=8.8 Hz, 1H), 7.33-7.37 (m, 1H), 7.22-7.27 (m, 2H), 7.10 (ddd, J=8.2, 2.6, 1.0 Hz, 1H), 6.90 (d, J=2.5 Hz, 1H), 6.65 (dd, J=8.8, 2.5 Hz, 1H), 4.76 (s, 1H), 3.85 (s, 3H), 3.84 (s, 3H).

(e) 2-Imino-3-cyano-7-methoxy-4-(3-methoxy-phenyl)-2H-thiochromene: To a mixture of (2-mercapto-4-methoxyphenyl)-(3'-methoxyphenyl)-methanone (35 mg, 0.13 mmol) and malononitrile (8.5 mg, 0.13 mmol) in approximately 200 μL of dry ethanol was added piperidine (7.0 μL, 0.06 mmol) at approximately 0° C. The resultant mixture was stirred at approximately 0° C. for approximately 2.5 h. The solvent was evaporated and the residue was purified by flash chromatography (silica gel, EtOAc:hexanes, 1:4) to yield 31 mg (75%) of 2-imino-3-cyano-7-methoxy-4-(3'-methoxy-phenyl)-2H-thiochromene-3-carbonitrile as an orange waxy oil. $^1$H NMR (CDCl$_3$): 9.31 (brs, 1H), 7.42-7.46 (m, 1H), 7.03-7.11 (m, 2H), 6.91 (d, J=7.8 Hz, 1H), 6.85-6.86 (m, 1H), 6.80 (bs, 1H), 6.68 (dd, J=9.1, 2.6 Hz, 1H), 3.85 (s, 3H), 3.84 (s, 3H).

EXAMPLE 31

2-Imino-3-cyano-7-dimethylamino-4-(3-bromo-4,5-dimethoxyphenyl)-2H-chromene

4 Å Molecular sieves (20 mg) were added to 2-amino-3-cyano-4-(3-bromo-4,5-dimethoxyphenyl)-4H-chromene (20 mg, 0.05 mmol) in dichloromethane (1 mL). The solution was stirred for approximately 15 min. Then 2,3-dichloro-5,6-dicyano-1,4-benzoquinone (10 mg, 0.05 mmol, 1 eq.) was added and stirred continuously at room temperature for approximately 1 h. The reaction mixture was diluted with ethyl acetate (20 mL) and washed with saturated aqueous sodium bicarbonate solution (20 mL) and brine (20 mL), and dried over sodium sulfate and concentrated to yield 17 mg (79%) of the desired compound. $^1$H NMR (DMSO-d$_6$): 8.33 (s, 1H), 7.28 (d, J=1.9 Hz, 1H), 7.21 (d, J=1.9 Hz, 1H), 6.87 (d, J=9.1 Hz, 1H), 6.56 (dd, J=2.5, 9.1 Hz, 1H), 6.40 (d, J=2.5 Hz, 1H), 3.84 (s, 3H), 3.82 (s, 3H), 3.03 (s, 6H).

EXAMPLE 32

3-Cyano-2-imino-7-methyl-4-(3-nitro-phenyl)-2H-pyrrolo[2,3-h]chromene

The title compound was prepared from 2-amino-3-cyano-7-methyl-4-(3-nitro-phenyl)-4H-pyrrolo[2,3-h]chromene by a procedure similar to that described in Example 11. $^1$H NMR (DMSO-d$_6$): 8.75 (s, 1H), 8.49-8.44 (m, 2H), 8.04 (dt, J=7.8, 1.5 Hz, 1H), 7.94 (t, J=8.1 Hz, 1H), 7.51 (d, J=3.0 Hz, 1H), 7.29 (d, J=9.0 Hz, 1H), 6.73-6.68 (m, 2H), 3.82 (s, 3H).

EXAMPLE 33

3-Cyano-2-imino-7-methyl-4-(3,4,5-trimethoxy-phenyl)-2H-pyrrolo[2,3-h]chromene

The title compound was prepared from 2-amino-3-cyano-7-methyl-4-(3,4,5-trimethoxy-phenyl)-4H-pyrrolo[2,3-h]chromene by a procedure similar to that described in Example 11. $^1$H NMR (DMSO-d$_6$): 8.61 (s, 1H), 7.49 (d, J=3.0 Hz, 1H), 7.32 (d, J=8.7 Hz, 1H), 6.92 (d, J=8.7 Hz, 1H), 6.87 (s, 2H), 6.71 (d, J=3.0 Hz, 1H), 3.82 (s, 9H), 3.78 (s, 3H).

EXAMPLE 34

3-Cyano-4-(3,5-dimethoxy-phenyl)-2-imino-7-methyl-2H-pyrrolo[2,3-h]chromene

The title compound was prepared from 2-amino-3-cyano-7-methyl-4-(3,5-dimethoxy-phenyl)-4H-pyrrolo[2,3-h]chromene by a procedure similar to that described in Example 4. $^1$H NMR (DMSO-d$_6$): 8.62 (s, 1H), 7.49 (d, J=3.3 Hz, 1H), 7.30 (d, J=9.0 Hz, 1H), 6.82 (d, J=8.7 Hz, 1H), 6.71-6.66 (m, 4H), 3.81 (s, 9H).

EXAMPLE 35

3-Cyano-2-imino-4-(3-methoxy-4,5-methylenedioxyphenyl)-7-methyl-2H-pyrrolo[2,3-h]chromene The title compound was prepared from 2-amino-3-cyano-7-methyl-4-(3-methoxy-4,5-methylenedioxyphenyl)-4H-pyrrolo[2,3-h]chromene by a procedure similar to that described in Example 11. $^1$H NMR (DMSO-d$_6$): 8.60 (s, 1H), 7.49 (d, J=3.3 Hz, 1H), 7.31 (d, J=9.0 Hz, 1H), 6.90 (d, J=9.0 Hz, 1H), 6.86 (d, J=1.5 Hz, 1H), 6.82 (d, J=1.5 Hz, 1H), 6.71 (d, J=3.3 Hz, 1H), 6.15 (d, J=3.0 Hz, 2H), 3.86 (s, 3H), 3.82 (s, 3H).

EXAMPLE 36

3-Cyano-2-imino-4-(3-methoxy-phenyl)-7-methyl-2H-pyrrolo[2,3-h]chromene

The title compound was prepared from 2-amino-3-cyano-4-(3-methoxy-phenyl)-7-methyl-4H-pyrrolo[2,3-h]chromene by a procedure similar to that described in Example 11. $^1$H NMR (DMSO-d$_6$): 8.63 (s, 1H), 7.55 (t, J=8.1 Hz, 1H), 7.49 (d, J=3.0 Hz, 1H), 7.30 (d, J=8.7 Hz, 1H), 7.18 (dd, J=2.7, 8.4 Hz, 1H), 7.10-7.06 (m, 2H), 6.77 (d, J=9.0 Hz, 1H), 6.71 (d, J=3.0 Hz, 1H), 3.83 (s, 3H), 3.81 (s, 3H).

EXAMPLE 37

3-Cyano-2-imino-4-(3-bromophenyl)-7-methyl-2H-pyrrolo[2,3-h]chromene

The title compound was prepared from 2-amino-3-cyano-4-(3-bromophenyl)-7-methyl-4H-pyrrolo[2,3-h]chromene by a procedure similar to that described in Example 11. $^1$H NMR (DMSO-d$_6$): 8.69 (s, 1H), 7.82 (dt, J=7.8, 1.8 Hz, 1H), 7.80 (m, 1H), 7.60 (dt, J=7.8, 0.6 Hz, 1H), 7.55 (dt, J=7.8, 1.5 Hz, 1H), 7.50 (d, J=3.3 Hz, 1H), 7.31 (dd, J=0.6, 7.3 Hz, 1H), 6.72-6.68 (m, 2H), 3.82 (s, 3H).

EXAMPLE 38

3-Cyano-7-methyl-4-(3-nitro-phenyl)-2-oxo-2H-pyrrolo[2,3-h]chromene

A solution of 3-cyano-2-imino-7-methyl-4-(3-nitro-phenyl)-2H-pyrrolo[2,3-h]chromene (31 mg, 0.087 mmol) 10% HCl (3 mL) and methanol (5 mL) was stirred at room temperature for 7 h. The reaction mixture was neutralized with 10% NaOH. The yellow precipitate was collected by vacuum filtration, washed with water, and dried in vacuo (24 mg, 77%). $^1$H NMR (acetone-$d_6$): 8.58-8.52 (m, 2H), 8.11 (dt, J=7.2, 0.9 Hz, 1H), 8.03 (dt, J=7.8, 0.9 Hz, 1H), 7.53 (d, J=3.3 Hz, 1H), 7.49 (dd, J=0.6, 8.7 Hz, 1H), 7.05 (d, J=8.7 Hz, 1H), 6.94 (dd, J=0.9, 3.3 Hz, 1H), 3.97 (s, 3H).

EXAMPLE 39

3-Cyano-4-(3,5-dimethoxy-phenyl)-7-methyl-2-oxo-2H-pyrrolo[2,3-h]chromene

The title compound was prepared from 3-cyano-4-(3,5-dimethoxy-phenyl)-2-imino-7-methyl-2H-pyrrolo[2,3-h]chromene by a procedure similar to that described in Example 38. $^1$H NMR (acetone-$d_6$): 7.50 (d, J=3.0 Hz, 1H), 7.48 (dd, J=0.9, 9.3 Hz, 1H), 7.15 (d, J=9.0 Hz, 1H), 6.90 (dd, J=0.9, 3.3 Hz, 1H), 6.74 (s, 3H), 3.97 (s, 3H), 3.89 (s, 6H).

EXAMPLE 40

3-Cyano-4-(3-methoxy-4,5-methylenedioxyphenyl)-7-methyl-2-oxo-2H-pyrrolo[2,3-h]chromene The title compound was prepared from 3-cyano-2-imino-4-(3-methoxy-4,5-methylenedioxyphenyl)-7-methyl-2H-pyrrolo[2,3-h]chromene by a procedure similar to that described in Example 38. $^1$H NMR (acetone-$d_6$): 7.50 (s, 1H), 7.48 (d, J=4.5 Hz, 1H), 7.24 (d, J=9.0 Hz, 1H), 6.92 (d, J=1.5 Hz, 1H), 6.90 (dd, J=0.6, 3.0 Hz, 1H), 6.81 (d, J=1.5 Hz, 1H), 6.18 (d, J=6.18 Hz, 2H), 3.97 (d, J=0.9 Hz, 3H), 3.96 (s, 3H).

EXAMPLE 41

3-Cyano-4-(3-methoxy-phenyl)-7-methyl-2-oxo-2H-pyrrolo[2,3-h]chromene

The title compound was prepared from 3-cyano-2-imino-4-(3-methoxy-phenyl)-7-methyl-2H-pyrrolo[2,3-h]chromene by a procedure similar to that described in Example 38. $^1$H NMR (acetone-$d_6$): 7.59 (dt, J=0.6, 8.1 Hz, 1H), 7.50 (d, J=3.3 Hz, 1H), 7.47 (dd, J=0.6, 8.7 Hz, 1H), 7.22 (ddd, J=0.9, 2.4, 8.4 Hz, 1H), 7.20-7.13 (m, 2H), 7.09 (d, J=9.0 Hz, 1H), 6.91 (dd, J=0:6, 3.3 Hz, 1H), 3.96 (s, 3H), 3.91 (3H).

EXAMPLE 42

3-Cyano-4-(3-bromo-phenyl)-7-methyl-2-oxo-2H-pyrrolo[2,3-h]chromene

The title compound was prepared from 3-cyano-2-imino-4-(3-bromo-phenyl)-7-methyl-2H-pyrrolo[2,3-h]chromene by a procedure similar to that described in Example 38. $^1$H NMR (acetone-$d_6$): 7.89-7.83 (m, 2H), 7.66-7.64 (m, 2H), 7.52-7.48 (m, 2H), 7.03 (d, J=9.0 Hz, 1H), 6,92 (dd, J=0.9, 3.3 Hz, 1H), 3.97 (s, 3H).

EXAMPLE 43

3-Cyano-7-methyl-4-(3,4,5-trimethoxy-phenyl)-2-oxo-2H-pyrrolo[2,3-h]chromene The title compound was prepared from 3-cyano-2-imino-4-(3,4,5-trimethoxy-phenyl)-7-methyl-2H-pyrrolo[2,3-h]chromene by a procedure similar to that described for Example 38. $^1$H NMR (acetone-$d_6$): 7.50 (d, J=3.0 Hz, 1H), 7.49 (dd, J=0.9, 9.0 Hz, 1H), 7.25 (d, J=8.7 Hz, 1H), 6.94 (s, 2H), 6.90 (dd, J=0.9, 3.3 Hz, 1H), 3.97 (s, 3H), 3.91 (s, 6H), 3.87 (s, 3H).

EXAMPLE 44

Identification of 3-Cyano-7-methoxy-4-(3-bromo-4,5-dimethoxyphenyl)-2-oxo-2H-chromene and Analogs as Caspase Cascade Activators and Inducers of Apoptosis in Solid Tumor Cells Human breast cancer cell lines T-47D and ZR-75-1 were grown according to media component mixtures designated by American Type Culture Collection +10% FCS (Invitrogen Corporation), in a 5% $CO_2$ –95% humidity incubator at 37° C. T-47D and ZR-75-1 cells were maintained at a cell density between 30 and 80% confluency at a cell density of 0.1 to $0.6 \times 10^6$ cells/mL. Cells were harvested at 600×g and resuspended at $0.65 \times 10^6$ cells/mL into appropriate media +10% FCS. An aliquot of 45 µl of cells was added to a well of a 96-well microtiter plate containing 5 µl of a 10% DMSO in RPMI-1640 media solution containing 0.16 to 10 µM of 3-cyano-7-methoxy-4-(3-bromo-4,5-dimethoxyphenyl)-2-oxo-2H-chromene (Example 1) or other test compound (0.016 to 1 µM final). An aliquot of 45 µl of cells was added to a well of a 96-well microtiter plate containing 5 µl of a 10% DMSO in RPMI-1640 media solution without test compound as the control sample. The samples were mixed by agitation and then incubated at 37° C. for 24 h in a 5% $CO_2$ –95% humidity incubator. After incubation, the samples were removed from the incubator and 50 µl of a solution containing 20 µM of N-(Ac-DEVD)-N'-ethoxycarbonyl-R110 fluorogenic substrate (SEQ ID NO:1) (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 µg/ml lysolecithin (Calbiochem) was added. The samples were mixed by agitation and incubated at room temperature. Using a fluorescent plate reader (Model 1420 Wallac Instruments), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3\ h)} - \text{Control } RFU_{(T=0)} = \text{Net } RFU_{(T=3\ h)}$$

The activity of caspase cascade activation was determined by the ratio of the net RFU value for 3-cyano-7-methoxy-4-(3-bromo-4,5-dimethoxy-phenyl)-2-oxo-2H-chromene, or other test compound, to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

CASPASE ACTIVITY AND POTENCY

| Example # Compound # | T-47D Ratio | T-47D EC50 (nM) | ZR-75-1 Ratio | ZR-75-1 EC50 (nM) |
|---|---|---|---|---|
| 1 | 6.2 | 257 | 4.2 | 97 |
| 2 | 4.1 | 44 | 5.4 | 11 |
| 3 | Inactive | Inactive | Inactive | Inactive |
| 4 | Inactive | Inactive | Inactive | Inactive |
| 5 | 2.0 | 200 | 10.4 | 111 |
| 6 | 9.1 | 4795 | 10.6 | 881.8 |
| 8 | 4.1 | 1172.2 | 10.1 | 878.2 |
| 9 | 4.4 | 4410.5 | 7.4 | 2048.7 |
| 16 | 3.1 | 105.5 | 3.6 | 173.5 |
| 17 | 8.9 | 99.7 | 11.7 | 43.4 |
| 18 | 2.2 | 1492.7 | 7.1 | 320.2 |
| 19 | 5.4 | 4059.7 | 7.9 | 556.3 |
| 20 | 1.6 | Inactive | 3.1 | 1000.0 |
| 21 | 5.8 | 545.8 | 9.1 | 279.0 |
| 22 | 1.5 | Inactive | 3.4 | 400.0 |
| 23 | 2.3 | 456.5 | 7.2 | 429.3 |
| 24 | 4.5 | 584.9 | 7.1 | 404.7 |
| 25 | 4.9 | 1091.4 | 6.1 | 356.1 |
| 26 | 1.9 | Inactive | 8.8 | 2767.8 |
| 28 | 2.2 | 2960.6 | | |
| 30 | Inactive | Inactive | Inactive | Inactive |
| 31 | 2500 | 2500 | | |
| 38 | 1.8 | >100 | 5.0 | 22 |
| 39 | 1.9 | >100 | 5.2 | 20 |
| 40 | 1.7 | >100 | 4.9 | 24 |
| 41 | 2.3 | 55 | 4.9 | 22 |
| 42 | 2.6 | 56 | 4.2 | 17 |

Thus, 3-cyano-7-methoxy-4-(3-bromo-4,5-dimethoxyphenyl)-2-oxo-2H-chromene (Example 1) and analogs are identified as potent caspase cascade activators and inducer of apoptosis in solid tumor cells.

Other active compounds with a fused-pyridine structure include the following compounds obtained from commercial sources.

| Cmp. # | Structure | Max efficacy T47D | Max efficacy ZR751 | EC50 (nM) T47D | EC50 (nM) ZR751 |
|---|---|---|---|---|---|
| 44 | | 10.7 | 19.2 | 3123 | 2037 |
| 45 | 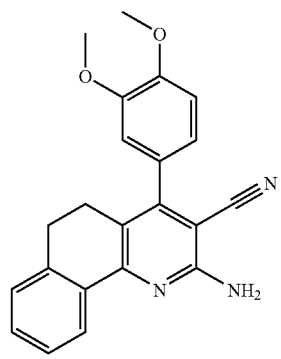 | Inactive | 7.0 | Inactive | 571 |

-continued

| Cmp. # | Structure | Max efficacy | | EC50 (nM) | |
|---|---|---|---|---|---|
| | | T47D | ZR751 | T47D | ZR751 |
| 46 | | Inactive | 3.1 | Inactive | 3407 |
| 47 | | Inactive | 2.7 | Inactive | 6111 |
| 48 | | Inactive | 2.9 | Inactive | 6040 |
| 49 | | Inactive | 4.8 | Inactive | 5712 |

-continued

| Cmp. # | Structure | Max efficacy | | EC50 (nM) | |
|---|---|---|---|---|---|
| | | T47D | ZR751 | T47D | ZR751 |
| 50 | | Inactive | 2.4 | Inactive | 576 |
| 51 | | Inactive | 2.8 | Inactive | 5385 |

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

3-Cyano-4-(3-methoxy-phenyl)-7-methoxy-2-oxo-2H-chromene;
7-Amino-4-(3-bromo-4,5-dimethoxyphenyl)-3-cyano-2-oxo-2H-chromene;
3-Cyano-7-dimethylamino-4-(3-bromo-4,5-dimethoxyphenyl)-2-oxo-2H-chromene;
7-Amino-3-cyano-4-(3,5-dimethoxyphenyl)-2-oxo-2H-chromene;

What is claimed is:
1. A compound selected from the group consisting of:
3-Cyano-7-methoxy-4-(3-bromo-4,5-dimethoxyphenyl)-2-oxo-2H-chromene;
3-Cyano-7-methoxy-4-(3,5-dimethoxyphenyl)-2-oxo-2H-chromene;
3-Cyano-7-dimethylamino-4-(3,5-dimethoxyphenyl)-2-oxo-2H-chromene;
4-(3-Bromo-4,5-dimethoxy-phenyl)-3-cyano-7-methylamino-2-oxo-2H-chromene;
7-Amino-4-(3-bromo-4,5-dimethoxy-phenyl)-3-cyano-2-imino-2H-chromene;

7-Bromo-4-(3-bromo-4,5-dimethoxy-phenyl)-3-cyano-2-imino-2H-chromene;

4-(3-Bromo-4,5-dimethoxy-phenyl)-7-chloro-3-cyano-2-oxo-2H-chromene;

4-(3-Bromo-4,5-dimethoxy-phenyl)-7-chloro-3-cyano-2-imino-2H-chromene; and

2-Imino-3-cyano-7-dimethylamino-4-(3-bromo-4,5-dimethoxyphenyl)-2H-chromene.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Fluorogenic substrate

<400> SEQUENCE: 1

Asp Glu Val Asp
1